United States Patent
Ishida et al.

(10) Patent No.: US 6,300,337 B1
(45) Date of Patent: Oct. 9, 2001

(54) ACETAMIDE DERIVATIVE AND USE THEREOF

(75) Inventors: Koichi Ishida, Ibaraki; Yoshikazu Suzuki, Tokyo, both of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/601,808

(22) PCT Filed: Feb. 16, 1999

(86) PCT No.: PCT/JP99/00657

§ 371 Date: Aug. 8, 2000

§ 102(e) Date: Aug. 8, 2000

(87) PCT Pub. No.: WO99/41277

PCT Pub. Date: Aug. 19, 1999

(30) Foreign Application Priority Data

Feb. 17, 1998 (JP) .................................................. 10-050038

(51) Int. Cl.$^7$ ....................... A61K 31/506; C07D 401/02; C07D 401/14
(52) U.S. Cl. ...................... 514/269; 544/300; 546/268.1; 514/274
(58) Field of Search ............................ 544/300; 514/269, 514/274; 546/268.1

(56) References Cited

FOREIGN PATENT DOCUMENTS

| 0 528 633 | 2/1993 | (EP) . |
| 8-143517 | 6/1996 | (JP) . |
| 10-53579 | 2/1998 | (JP) . |
| 98/21210 | 10/1993 | (WO) . |
| 93/25574 | 12/1993 | (WO) . |
| 98/09949 * | 3/1998 | (WO) . |
| 98/18794 | 5/1998 | (WO) . |

OTHER PUBLICATIONS

Circulation Research, vol. 66, No. 4, Apr. 1990; Hidenori Urata, et al.; "Angiotensin II–Forming Pathways in Normal and Failing Human Hearts".

Journal of Cellular BioChemistry 38: 291–301 (1988) Cellular Proteases and Control Mechanisms 13–23; Nobuhiko Katunuma, et al.; "Biological Functions of Serine Proteases in Mast Cells in Allergic Inflammation".

Archives of BioChemistry and BioPhysics vol. 312, No. 312, No. 1, Jul., pp. 67–74, 1994; Youichi Matsunaga, et al.; "Inhibitors of Chymotrypsin–like Proteases Inhibit Eosinophil Peroxidase Release from Activated Human Eosinophils".

Proc. Natl. Acad. Sci. USA vol. 84, pp. 364–367, Jan. 1987 BioChemistry; Hai Le Trong et al.; "Substrate Specificity of the Chymotrypsin–like Protease in Secretory Granules Isolated from Rat Mast Cells".

Journal of Medicinal Chemistry, 1977, vol. 20, No. 4; Rinzo Nishizawa, et al.; "Synthesis and Structure–Activity Relationships of Bestatin Analogues, Inhibitors of Amiopeptidase B".

J.Org. Chem., vol. 43, No. 18, 1978 pp. 3624–3626.

Peptide Chemistry 1994: M.Ohno (Ed.) Protein Research Foundation, Osaka (1995); pp. 169–172; Hiroaki Taguchi, et al.; "Facile Synthesis of 2(1H)–Pyrazinone Derivatives from Dipeptides".

Chemical Abstracts vol. 97, 1982 (97:162945s) and Chem. Ber. 115, 2807–2818 (1982); "Synthese von Cyclopenta[e]–1,2,4–triazinen".

Peptide Chemistry 1995; N.Nishi (Ed.), Protein Research Foundation, Osaka (1996) pp. 289–292; Hiroaki Taguchi, et al.; "Synthesis of 2(1H)–Pyrazinone Derivatives from Dipeptides and Its Application to the Development of Proteinase Inhibitor".

J.Med.Chem. 1995, 38,98–108; Chris A. Veale, et al.; "Nonpeptidic Inhibitors of Human Leukocyte Elastase. 5. Design, Synthesis, and X–ray Crystallography of a Series of Orally Active 5–Aminopyrimidin–6–one–Containing Trifluoromethyl Ketones".

J. Org. Chem. 1993, 58, 4490–4493; Chris A. Veale, et al.; "Efficient Method for the Synthesis of 1,4–Disubstituted 5–Carbomethoxypyrimidin–6–ones".

Copy of the International Search Report dated May 11, 1999.

* cited by examiner

Primary Examiner—Alan L. Rotman
Assistant Examiner—Rita Desai
(74) Attorney, Agent, or Firm—Nields & Lemack

(57) ABSTRACT

The present Invention relates to a novel acetamide derivative represented by the following Formula 1, which has an inhibition activity for chymotrypsin type proteases and is useful as an inhibitor for the above enzyme, especially as an inhibitor for chymase, and the use thereof as a medicine, for example, an antiasthma drug or a drug for curing vascular injuries complicated with angiogenesis and atheroma.

Formula 1

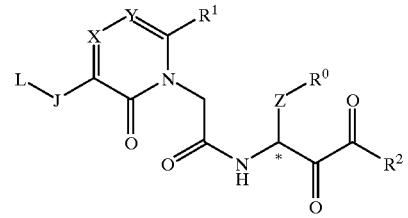

wherein $R^0$ represents a substituted or unsubstituted phenyl group, $R^1$ represents an aryl group, a heteroaryl or an aliphatic lower alkyl group with or without substituents, $R^2$ represents a substituted or unsubstituted alkyl, an aryl alkyl, a heteroaryl alkyl, and a heteroaryloxy alkyl or the like, J represents a carbonyl group, or a methylene group or the like, L represents a methoxy, hydroxyl or acetyloxy group or the like, X and Y independently represents a nitrogen atom or a carbon atom, Z represents a methylene group or a polyethylene group optionally having a substituent.

9 Claims, No Drawings

ACETAMIDE DERIVATIVE AND USE THEREOF

This application is a national stage filing under 35 USC 371 from PCT/JP99/00657, filed Feb. 16, 1999.

DESCRIPTION

1. Technical Field

The present invention relates to a heterocyclic compound having substituents containing a consecutive dicarbonyl structure, particularly to a 1-pyrimidinylacetamide compound, an 1-pyrazinylacetamide compound, a 4-triazinylacetamide compound, and relates to an inhibitor for chymotrypsin type proteases. The present compound is useful as a preventive or therapeutic agent for diseases in which chymotrypsin type proteases are generally considered to participate. For example, chymotrypsin type proteases are considered to participate directly or indirectly in diseases such as asthma, allergy, inflammations, rheumatism, hypertension, heart failure, myocardial infarction, cardiac hypertrophy, vascular injuries complicated with angiogenesis and atheroma, nephritis and renal failure. The present invention encompasses an intermediate useful for synthesis of the heterocyclic amide compound having a consecutive dicarbonyl structure, a process for producing said heterocyclic amide compound, a pharmaceutical composition containing said heterocyclic amide compound as the active ingredient, and a pharmaceutical use of said heterocyclic amide compound for the treatment of humane diseases, particularly for the treatment of the above diseases.

2. Background Art

It is known that chymase belongs to chymotrypsin type proteases among serine proteases and is a cytotoxic protein accumulated in secretory granules in mast cells and released upon stimulation. Further, it is recently reported in Circ. Res., 66, 883 (1994) that chymase possesses the action of converting angiotensin I into angiotensin II involved in blood pressure regulation in vivo. Further, it is also known that a chymase inhibitor inhibits release of histamine from mast cells (J. Cell. Biochem., 38, 291 (1988)) and release of a cytotoxic protein from eosinophils (Arch. Biochem. Biophys., 312, 67, (1994)). That is, it is known generally at present that chymase is involved not only in cytotoxicity but also in release of various mediators in vivo.

Further, the action of chymase varies depending on the type of animal, and it is reported that there is a great difference in the action particularly between human or dog and rodent (Proc. Natl. Acad. Sci. USA, 84, 364 (1987)).

As a compound inhibiting chymase, only an inhibitor for chymotrypsin as a digestive enzyme is known at present and is not satisfactory in inhibitory activity, selectivity of inhibition toward other proteases, stability of the compound in vivo, toxicity etc. and it has not been developed as a pharmaceutical composition. Accordingly, there is demand for a highly safe chymase inhibitor which at low concentration, selectively inhibits chymase.

DISCLOSURE OF THE INVENTION

Under these circumstances, the present inventors made extensive studies to find chymase inhibitors in order to solve the above problems, and as a result, they arrived at the present invention.

That is, the present invention relates to the following items 1 to 13:

1. A novel acetamide derivative represented by the following Formula 1 or the pharmacologically acceptable salt thereof.

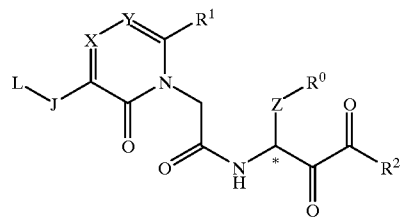

Formula 1 wherein $R^0$ is a phenyl group whose ring may have one or more substituent groups selected from the group consisting of a halogen, a hydroxyl group, a lower alkoxy group, a lower alkyl group, and a halogenomethyl group defined as group A;

$R^1$ is (1) an aryl group, (2) a heteroaryl group or (3) a 1–6C straight-chain, branched or cyclic alkyl group, which may independently have one or more substituent groups defined as group A; or $R^1$ may have one or more substituent groups selected from the group consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$ and $P(O)(OR_a)_2$ as defined as group B on the above groups (1) to (3) (where each $R_a$ to $R_c$ is independently a hydrogen, a lower or a substituted lower alkyl; or each $R_a$ to $R_c$ is independently an aryl (1–7C) alkyl group, a heteroaryl (1–7C) alkyl, an aryl and a heteroaryl, among which the aryl or the heteroaryl may have one or more, usually 1 to 3, substituent groups selected from the group of above-defined group A on the ring; or $R^1$ may have one or more substituent groups defined below as cyclic group G on the above groups (1) to (3) (cyclic group G; cyclic group G represents a heterocyclic group consisting of a 5- or 6-membered ring containing 1 to 3 oxygen or nitrogen atoms and may have substituent groups);

$R^2$ represents a (1–8C)alkyl, an aryl (1–7C) alkyl group, a heteroaryl (1–7C)alkyl, and an aryl; or $R^2$ represents the above-defined group B or a (1–8C) alkyl having the group B as a substituent group; or a (1–8C) alkyl having the above-defined cyclic group G as a substituent group;

X and Y independently represents a nitrogen atom or a carbon atom and may be substituted by groups represented by above-mentioned $R_a$ to $R_c$;

Z represents a methylene group or a polymethylene group, and may have substituents;

J represents a carbonyl group, or a methylene group whose two hydrogens may be independently substituted by above-mentioned $R_a$ or $R_b$;

L represents an amino group as shown by $R^3 R_aN$, or $R^3 O$ where $R^3$ is a hydrogen; or $R^3$ is (1) $D(CH_2)_{0-3}.CO$, (2) $D.CO.E.CO$ or (3) $D.SO_2.E.CO$ as an acyl group; or $R^3$ is $D(CH_2)_{0-3}.SO_2$ or $D.CO.E. SO_2$ as a sulfonyl group (wherein group D represents a hydrogen, a 1–6C straight-chain, branched or cyclic alkyl group, trifluoromethyl, 2,2,2-trifluoroethoxy, amino, methoxyamino, 2,2,2-trifluoroethylamino, $R_bR_cN$, $R_bR_cN.O$, $R_aO$, $R_a$, $R_aOCO$, $R_bR_cNCO$, $R_aSO_2NR_b$, $R_aS$ and the above-defined group G; and group E represents a divalent crosslinking group containing 1 to 6 carbon atoms, and may contain 1–3 hetero atoms selected from the group of oxygen, nitrogen and sulfur); or $R^3$ is a thiourea represented by $R_bR_cN.CS$; or $R^3$ is an urea represented by $R_bR_cN.CO$; or $R^3$ is $R_a$. $R_a$ to $R_c$ show the same respective meanings as defined in $R^1$.

2. A novel acetamide derivative or the pharmacologically acceptable salt thereof according to the above item 1, wherein said $R^0$, $R^1$, $R^2$, X, Y, Z, J, and in Formula 1 are the respective followings:

$R^0$ is a phenyl group whose ring may have 1–3 substituent groups selected from the group consisting of a halogen, a hydroxyl group, a lower alkoxy group, a lower alkyl group, and a halogenomethyl group defined as group A;

$R^1$ is a phenyl group whose ring may have one substituent group above-defined as group A; or $R^1$ is a phenyl group whose ring may have one substituent group selected from the group consisting of $OR_a$, $COOR_a$, $CONR_bR_c$, $NR_bR_c$, $NR_bCHO$, $NR_bCOR_a$, $SO_2OR_a$, $SO_2R_a$, $CONR_bSO_2R_a$ and $P(O)(OR_a)_2$ as defined as group B (where each $R_a$ to $R_c$ is independently a hydrogen, a lower or a substituted lower alkyl; or each $R_a$ to $R_c$ is independently an aryl (1–3C) alkyl, a heteroaryl (1–3C) alkyl, an alkyl, an aryl and a heteroaryl, among which the aryl or the heteroaryl may have one substituent group selected from the group of above-defined group A on the ring).

$R^2$ represents a (1–4C) alkyl, an aryl (1–3C) alkyl, a heteroaryl (1–3C) alkyl, and an aryl; or R represents the above-defined group B or a (1–3C) alkyl having group B as a substituent group; or a (1–3C) alkyl group having the above-defined cyclic group G as a substituent group, where the cyclic group G represents a cyclic group selected from the group consisting of piperazin-1-yl which may have a lower alkyl group or an arylmethyl group at the 4-position, pyrrolidin-1-yl, piperidin-1-yl, 4-morpholin-1-yl, 2-oxo-1,2-dihydropyridin-1-yl, pyridyloxy, pyrazyloxy, pyridazyloxy, and pyrrol-1-yl;

X and Y independently represents a nitrogen atom or an unsubstituted carbon atom;

Z represents a methylene group;

J represents a carbonyl group, or a methylene group;

L represents $R^3$ O or an amino group as shown by $R^3$ $R_aN$ where $R^3$ is a hydrogen; or $R^3$ is (1) $D.(CH_2)_{0-3}.CO$, (2) $D.CO.E.CO$ or (3) $D.SO_2.E.CO$ as an acyl group; or $R^3$ is $D.(CH_2)_{0-3}.SO_2$ or $D.CO.E.SO_2$ as a sulfonyl group (wherein group D represents a hydrogen, a C1–C3 straight-chain, branched or cyclic alkyl group, trifluoromethyl, 2,2,2-trifluoroethoxy, 2,2,2-trifluoro ethylamino, $COOR_a$, $CONR_bR_c$, N $R_bR_c$ or the above-defined group G; and group E represents a phenylene, a heteroarylene 1,4-piperazine-di-yl, cyclohexylene, or 1,4-cyclohexa dienylene); or $R^3$ is a thiourea represented by $R_bR_cN.CS$; or $R^3$ is an urea represented by $R_bR_cN.CO$; or $R^3$ is $R_a$; $R_a$ shows the same meaning as defined above.

3. A novel acetamide derivative or the pharmacologically acceptable salt thereof according to the above item 1, wherein $R^0$ is a phenyl group whose ring may have 1–4 substituent groups defined as group A; $R^1$ is a phenyl, a furyl, a thienyl, or a pyridyl whose ring may have 1–2 substituent groups defined as group A; $R^2$ represents methyl, butyl, phenylpropyl, 4-morpholin-1-yl-propyl, 1-(ethoxycarbonyl) propyl, 4-methylpiperazin-1-yl-propyl, 2-oxo-1,2-dihydro pyridin-1-yl-propyl, or (2-pyridyloxy)propyl; each X and Y represents a nitrogen atom or an unsubstituted carbon atom;

Z represents a methylene group; J represents a methylene group;

L represents methoxy, hydroxyl, or acetyloxy, provided that the group A represents a group selected from the group consisting of a halogen, a hydroxyl group, a lower alkoxy group, a lower alkyl group and a halogenomethyl group.

4. A novel acetamide derivative or the pharmacologically acceptable salt thereof according to the above item 1, wherein $R^0$ and $R^1$ are unsubstituted phenyl groups; $R^2$ is (2-pyridyloxy)propyl; X is a carbon atom; Y is a nitrogen atom; Z and J are methylene groups; L is a lower alkyl or a lower alkylcarbonyloxy.

5. A novel acetamide derivative or the pharmacologically acceptable salt thereof according to the above item 1, wherein said acetamide derivative is a compound selected from the group consisting of:

(A) 2-(5-acetyloxymethyl-4-oxo-2-phenyl-3,4-dihydro-pyrimidin-3-yl)-N-{2,3-dioxo-1-phenylmethyl-6-(2-pyridyl-oxy)}hexylacetamide, (B) 2-(5-hydroxymethyl-4-oxo-2-phenyl-3,4-dihydropyrimidin-3-yl)-N-{2,3-dioxo-1-phenylmethyl-6-(2-pyridyloxy)}hexyl acetamide, (C) 2-(5-methoxymethyl-4-oxo-2-phenyl-3,4-dihydropyrimidin-3-yl)-N-{2,3-dioxo-1-phenylmethyl-6-(2-pyridyloxy)}hexyl acetamide, (D) 2-(5-ethoxycarbonyl-4-oxo-2-phenyl-3,4-dihydropyrimidin-3-yl)-N-{2,3-dioxo-1-phenylmethyl-6-(2-pyridyloxy)}hexyl acetamide, (E) 2-(5-acetylaminomethyl-4-oxo-2-phenyl-3,4-dihydro-pyrimidin-3-yl)-N-{2,3-dioxo-1-phenylmethyl-6-(2-pyridyl-oxy)}hexylacetamide, (F) 2-(5-methylsulfonylaminomethyl-4-oxo-2-phenyl-3,4-dihydropyrimidin-3-yl)-N-{2,3-dioxo-1-phenylmethyl-6-(2-pyridyloxy)}hexylacetamide, (G) 2-(5-formylaminomethyl-4-oxo-2-phenyl-3,4-dihydro-pyrimidin-3-yl)-N-{2,3-dioxo-1-phenylmethyl-6-(2-pyridyl-oxy)}hexylacetamide, (H) 2-(4-oxo-2-phenyl-5-phenylmethylaminosulfonylaminomethyl-3,4-dihydropyrimidin-3-yl)-N-{2,3-dioxo-1-phenylmethyl-6-(2-pyridyloxy)}hexylacetamide, (I) 2-(4-oxo-2-phenyl-5-phenylmethylsulfonylaminomethyl-3,4-dihydropyrimidin-3-yl)-N-{2,3-dioxo-1-phenylmethyl-6-(2-pyridyloxy)}hexylacetamide, (J) 2-{4-oxo-2-phenyl-5-(2-pyridyl)methylaminosulfonylaminomethyl-3,4-dihydropyrimidin-3-yl}-N-{2,3-dioxo-1-phenylmethyl-6-(2-pyridyloxy)}hexylacetamide, (K) 2-{5-(2-pyridine)carbonylaminomethyl-4-oxo-2-phenyl-3,4-dihydropyrimidin-3-yl}-N-{2,3-dioxo-1-phenylmethyl-6-(2-pyridyloxy)}hexylacetamide, and (L) 2-(4-oxo-2-phenyl-5-phenylmethylaminosulfonylaminomethyl-3,4-dihydropyrimidin-3-yl)-N-{2,3-dioxo-1-phenylmethyl-6-(2-oxo-1,2-dihydropyridin-1-yl)}hexylacetamide.

6. A salt of the novel acetamide derivative according to the above item 1, wherein said salt is (A) selected from the group consisting of the alkali metal salt, the alkaline earth metal salt, the aluminum salt, the ammonium salt and the salt obtained by reacting with an organic base forming the pharmaceutically acceptable cations if the novel acetamide derivative of Formula 1 is an acidic compound, or (B) selected from the group consisting of acid addition salts obtained by reacting with acids forming the pharmaceutically acceptable anions if the novel acetamide derivatives of Formula 1 is a basic compound.

7. A process for producing the novel acetamide derivative according to any of the above items 1 to 6 or the pharmacologically acceptable salt thereof, which comprises the following step (A) and/or (B):
(A) the step of oxidizing the alcohol compound of Formula 2:

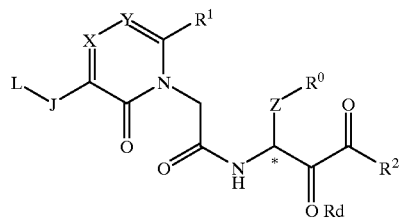

Formula 2 after removal of a protective group of alcohol if present, to convert it into the novel acetamide derivative of Formula 1 (wherein Rd represents a hydrogen or a protective group for hydroxyl group) and/or
(B) the step of condensation of the compound of Formula 3

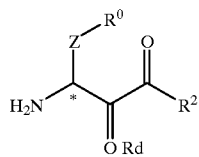

Formula 3 with the compound of Formula 4 or the salt thereof

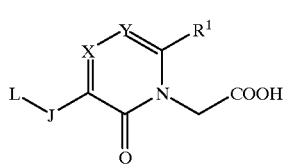

Formula 4

(wherein $R^0$, $R^1$, $R^2$, X, Y, Z, J and L represent the same respective groups as defined in the above item 1. Rd shows the same meaning as above-mentioned).
8. A compound represented by Formula 2 or the salt thereof:

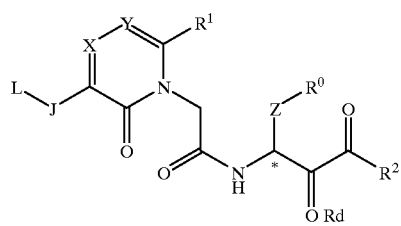

Formula 2

(wherein $R^0$, $R^1$, $R^2$, X, Y, Z, J and L represent the same respective groups as defined in the above item 1 and Rd is a hydrogen or a protective group for a hydroxyl group).

9. A compound represented by Formula 3 or the reactive carboxylic derivative thereof:

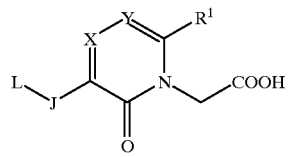

Formula 3

(wherein $R^1$, X, Y, J and L represent the same respective groups as defined in the above item 1).

10. A pharmaceutical composition comprising the novel acetamide derivative according to any of the above items 1 to 6 or the pharmacologically acceptable salt thereof as an active ingredient.

11. An antiathmatic agent, an antiallergic agent, an anti-inflammatory agent, an antiphlogistic, an antirheumatic agent, an antihypertensive agent, an anti-heart failure agent, an anti-myocardial infarction agent, a remedy for cardiac hypertrophy or vascular injuries complicated with angiogenesis or atheroma, an anti-nephritis agent, an anti-renal failure agent, or their prophylactic agents comprising the novel acetamide derivative according to any of the above items 1 to 6 or the pharmacologically acceptable salt thereof as an active ingredient.

12. A novel protease inhibitor comprising the novel acetamide derivative according to any of the above items 1 to 6 or the pharmacologically acceptable salt thereof as an active ingredient.

13. A novel chymase inhibitor comprising the novel acetamide derivative according to any of the above items 1 to 6 or the pharmacologically acceptable salt thereof as an active ingredient.

BEST MODE FOR CARRYING OUT THE INVENTION

The present invention relates to a novel acetamide derivative having substituents containing a consecutive dicarbonyl structure, and particularly to a 3-pyrimidinylacetamide compound, an 4-pyrazinylacetamide compound, and a 4-triazinylacetamide compound or their respective salts (hereinafter referred to as the present compound), and to a medical use of the present compound for treating diseases in a warm-blooded animal including human. A protease inhibitor comprising the present compound as an active ingredient, which has an inhibitory action on the leukocyte activation of mast cell or eosinophils as well as an inhibitory action on production of angiotensinII, is expected as an agent for treating or preventing diseases such as asthma, allergy, inflammation, rheumatism, hypertension, heart failure, myocardial infarction, cardiac hypertrophy, vascular injuries complicated with angiogenesis and atheroma, nephritis and renal failure.

In the present specification, the following definitions are used unless otherwise specified.

Halogen means fluorine, chlorine, bromine and iodine.

Alkyl and alkoxy are of straight-chain or branched-chain (generally, propyl means a straight-chain propyl and isopropyl means a branched propyl; however, propyl shall include both the propyl in the present specification if no problem).

The lower alkyl group or the lower alkoxy group represents a C1–C6 branched or straight-chain group. The lower acyloxy is a C1 to about C6 group. The aryl represents a phenyl group, or a C9–C10 monocyclic or hetero carbocyclic group (excluding a hetero-aromatic group) which contains at least one benzene condensed at the ortho-position to give the fused ring. A heteroaryl contains carbon atoms and 1 to 4 heteroatoms selected from the group consisting of oxygen, nitrogen and sulfur, and represents a 5 to 6-membered monocyclic hetero-aromatic group or an 8 to 10-membered polycyclic heterocyclic group which contains an aromatic ring condensed at the ortho-position to give the fused ring.

Since mutually asymmetrical substituents may bind to the carbon atom at the position of the chiral center indicated by "*" in Formula 1, the compound of Formula 1 exists as a single optical isomer or a racemate. The compound of formula 1, if it contains an additional one chiral element, exists as a single diastereomer or a mixture of diastereomers. Any of these compounds may be isolated. The compound of Formula 1 in the present invention includes the individual diastereomer and the mixture of diastereomers and further the compound of Formula 1 includes the individual enantiomer and the mixture of enantiomers.

As can be understood by those skilled in the art, the consecutive dicarbonyl structure in Formula 1 can exist as a solvate, particularly a hydrate. Accordingly, the compound of Formula 1 in the present invention includes a solvate thereof.

The compound of Formula 1 can indicate a variety of polymorphism such as tautomerism, in addition to the above-described solvate. Accordingly, the present invention encompasses any compound of formula 1 having inhibitory action on chymotrypsin-like enzyme regardless of a form of polymorphism such as a racemate, an optical isomer and a solvate.

The examples of a functional group in the present invention will be described below for an illustrative purpose, but the present invention shall not be limited to these examples.

The lower alkyl group includes methyl group, ethyl group, n- or i-propyl group, n-, i- or t-butyl group, straight-chain or branched pentyl group and straight-chain or branched hexyl group. A C1–C4 alkyl group is preferable.

The lower alkoxy group includes methoxy group, ethoxy group, n- or i-propoxy group, n-, i- or t-butoxy group, straight-chain or branched pentyloxy group and straight-chain or branched hexyloxy group. A C1–C5 alkyl group is preferable.

The aryl includes phenyl, naphthyl, benzopyperazinyl, and chromanyl group. Phenyl is preferable.

The heteroaryl includes imidazolyl, oxazolyl, furyl, thienyl, pyridyl, pyrimidinyl, and triazinyl group. Pyridyl group or pyrimidinyl group is preferable.

The group A includes fluorine, chlorine, bromine, hydroxyl group, the above lower alkyl, the above alkoxy, mono-, di- or trichloromethyl, mono-, di- or trifluoromethyl group, or mono-, di- or tribromomethyl etc. The preferable examples of the group A are fluorine, chlorine, bromine, hydroxyl group, methyl, ethyl and methoxy. $R_a$, $R_b$ or $R_c$ includes for example hydrogen; a lower alkyl such as methyl, ethyl, propyl, butyl and isopropyl; an aryl(1–7C) alkyl such as benzyl, phenethyl and phenylpropyl; a heteroaryl(1–7C)alkyl such as pyridylmethyl, pyridylethyl, pyridylpropyl, furylmethyl, furylethyl and furylpropyl; an aryl such as phenyl and halogeno-substituted phenyl; a heteroaryl such as pyridyl, pyrimidinyl, furyl group and thienyl group.

$OR_a$ in the group B or the group D etc. includes for example hydroxyl,methoxy, ethoxy, propyloxy, isopropyloxy, butoxy, benzyloxy, pyridylmethyloxy, phenoxy and pyridyloxy etc.

$COOR_a$ in the group B or the group D etc. includes for example methoxycarbonyl, ethoxycarbonyl, propyloxycarbonyl, isopropyloxycarbonyl, butoxycarbonyl, benzyloxycarbonyl, pyridylmethyloxycarbonyl and phenoxycarbonyl etc.

$CONR_bR_c$ in the group B or the group D etc. includes dimethylaminocarbonyl, methylethylaminocarbonyl, diethylaminocarbonyl and dipropylaminocarbonyl etc.

$NR_bR_c$ in the group B or the group D etc. includes for example monomethylamino, dimethylamino, methylethylamino, diethylamino and dipropylamino etc.

$NR_bCHO$ in the group B etc. is preferable for example formylamino and N-formyl-N-methylamino etc.

$NR_bCOR_a$ in the group B etc. includes for example acetylamino, benzoylamino, butyrylamino and N-acetyl-N-methylamino etc.

$SO_2OR_a$ in the group B etc. includes for example sulfonic acid group etc.

$SO_2R_a$ in the group B etc. includes for example methylsulfonyl, ethylsulfonyl, propylsulfonyl, butylsulfonyl, benzylsulfonyl, toluenesulfonyl, benzenesulfonyl, formaminobenzenesulfonyl, nitrobenzenesulfonyl, methoxybenzenesulfonyl, pyridylsulfonyl, pyridylmethylsulfonyl and trifluoromethylsulfonyl etc.

$CONR_bSO_2R_a$ in the group B etc. includes for example methyl-sulfonylaminocarbonyl, phenylsulfonylaminocarbonyl and phenylmethylsulfonylaminocarbonyl etc.

$P(O)(OR_a)_2$ in the group B etc. includes for example diethylphosphono, diphenylphosphono and dibenzylphosphono etc.

The preferable examples of the group B are methoxy, ethoxy, propyloxy, isopropyloxy, phenylmethyloxy, phenethyloxy, phenylpropyloxy, pyridylmethyloxy, pyridylethyloxy, pyridylpropyloxy, furylmethyloxy, furylethyloxy, furylpropylyloxy, pyridyloxyethyloxy and pyridyloxypropyloxy.

Group E represents a C1–C6 divalent crosslinking group which may contain 1 to 3 heteroatoms selected from the group consisting of oxygen, nitrogen and sulfur, and includes a divalent benzene nucleus such as phenylene; a divalent heteroaryl nucleus such as heteroarylene, 1,4-piperazine-di-yl; a divalent C1–C6 straight-chain or branched aliphatic crosslinking group such as methylene, dimethylene, trimethylene, 2-methyltrimethylene; or an alicyclic crosslinking group such as cyclohexylene, 1,4-cyclohexadienylene etc.

Group G includes for example a 5- to 6-membered heteroaryl or a 5- to 6-membered heteroatom-containing alicyclic group. Preferable are 4-morpholine-4-yl, 4-methylpiperazin-1-yl, pyrrolidin-1-yl, piperidin-1-yl pyrrol-1-yl and 2-oxo-1,2-dihydropyridin-1-yl, 2-pyridyloxy, pyradyloxy and pyridazyloxy.

Preferable examples of group D are hydrogen, methyl, cyclohexyl, phenyl, pyridyl, trifluoromethyl, 2,2,2-trifluoroethyloxy, methyloxyamino, 2,2,2-trifluoroethylamino and phenylmethylamino etc.

The preferable example of $R^0$ is a phenyl group whose ring may have 1 to 4 substituent groups selected from the group consisting of a halogen, hydroxyl group, a lower alkoxy, a lower alkyl, and trifluoromethyl defined as group A.

The preferable examples of $R^1$ are phenyl, furyl, thienyl or pyridyl group whose rings may have 1 or 2 substituent groups defined as group A. More preferable is phenyl group.

The preferable examples of $R^2$ are a (1–4C) alkyl, an aryl (1–3C) alkyl and a G(1–3C) alkyl having the previously defined group G as a substituent group. More preferable are methyl, ethyl, propyl, butyl, isopropyl, phenylmethyl, phenethyl, phenylpropyl, pyridylmethyl, pyridylethyl, pyridylpropyl, furylmethyl, furylethyl, furylpropyl, pyridyloxymethyl, pyridyloxyethyl and pyridyloxypropyl group; or piperazin-1-yl-(1–3C) alkyl which may have a substituent group selected from the group consisting of methyl, ethyl, propyl, butyl, isopropyl, benzyl or pyridylmethyl at the 4-position, piperidin-1-yl-(1–3C) alkyl, 4-morpholine-1-yl-(1–3C) alkyl, pyrrolidin-1-yl-(1–3C) alkyl, 2-oxo-1,2-dihydropyridin-1-yl-(1–3C) alkyl, methoxycarbonyl (C0–3C) alkyl, ethoxycarbonyl (0–3C) alkyl, propyloxycarbonyl (0–3C) alkyl, butyloxycarbonyl (0–3C) alkyl, benzyloxycarbonyl (0–3C) alkyl, t-butoxycarbonyl (0–3C) alkyl, phenyloxycarbonyl (0–3C) alkyl, nitrophenyloxycarbonyl (0–3C) alkyl, and bromophenyloxy-carbonyl (0–3C) alkyl, 2-pyridyloxy(1–3C)alkyl and 4-methyl piperazin-1-yl-carbonyl(1–3C) alkyl . More preferable are methyl, ethyl, propyl, butyl, phenylpropyl, 4-morpholin-1-yl (1–3C) alkyl, 2-oxo-1,2-dihydro pyridin-1-yl (1–3C) alkyl, 2-pyridyloxy (1–3C) alkyl, ethoxycarbonyl (0–3C) alkyl, and 4-methylpiperazin-1-yl-carbonyl (1–3C) alkyl.

The particularly useful element of X and Y is carbon or nitrogen.

The particularly useful group of Z is methylene group.

The particularly useful group of J is carbonyl group or methylene group.

If L is $R^3R_aN$, $D(CH_2)_{0-3}$.CO as $R^3$ includes formyl, acetyl, propionyl, cyclopropanecarbonyl, valeryl, butyryl, cyclopropylmethylcarbonyl, pivaloyl, trifluoroacetyl, phenylacetyl, 3-phenyl-propionyl, pyridylcarbonyl, benzoyl, tetrahydro-2-furoyl, tetrahydro-3-furoyl, methoxycarbonyl, ethoxycarbonyl, propyloxycarbonyl, isopropyloxycarbonyl, butyloxycarbonyl, benzyloxycarbonyl, 9-fluorenyloxycarbonyl, 2,2,2-trichloroethoxycarbonyl, allyloxycarbonyl, and hydroxyoxalyl etc.

If L is $R^3 R_aN$, the acyl group D.CO.E.CO or $D.SO_2.E.CO$ as $R_3$ includes 4-{1-(4-morpholin)carbonyl} benzenecarbonyl, {4-(1-pyrrolidin-1-yl) carbonyl} benzenecarbonyl, and {4-(1-piperidin-1-yl)carbonyl} benzenecarbonyl etc.

If L is $R^3 R_aN$, $D(CH_2)_{0-3}.SO_2$ as $R^3$ includes toluenesulfonyl, benzenesulfonyl, formaminobenzenesulfonyl, nitrobenzenesulfonyl, methoxybenzenesulfonyl, pyridylsulfonyl, pyridylmethylsulfonyl, methylsulfonyl, ethylsulfonyl, propylsulfonyl, butylsulfonyl, benzylsulfonyl, trifluoromethylsulfonyl, phenacylsulfonyl, aminosulfonyl, dimethylaminosulfonyl, diethylaminosulfonyl, phenylaminosulfonyl, benzylaminosulfonyl, pyridylaminosulfonyl, and pyridylmethylaminosulfonyl etc.

If L is $R^3R_aN$, the thiourea $R_bR_cN.CS$ as $R^3$ includes methylaminothiocarbonyl, ethylaminothiocarbonyl, propylaminothiocarbonyl, butylaminothiocarbonyl, isopropylaminothiocarbonyl, valerylaminothiocarbonyl, benzylaminothiocarbonyl etc.

If L is $R^3R_aN$, the urea $R_bR_cNCO$ as $R^3$ includes methylaminocarbonyl, ethylaminocarbonyl, propylaminocarbonyl, butylaminocarbonyl, isopropylaminocarbonyl, valerylaminocarbonyl and benzylaminocarbonyl etc.

If L is $R^3O$, the $R^3$ is the same as described in the case that L is $R^3R_aN$; however the particularly preferable $R^3$ if L is $R^3O$ includes hydrogen; a lower alkyl such as methyl, ethyl, propyl, butyl and isopropyl; an aryl (1–7C) alkyl group such as benzyl, phenethyl and phenylpropyl etc; a heteroaryl (1–7C) alkyl such as pyridylmethyl, pyridylethyl, pyridylpropyl, furylmethyl, furylethyl and furylpropyl etc; an aryl such as phenyl and halogen-substituted phenyl etc; a heteroaryl such as pyridyl, pyrimidinyl, furyl and thienyl group; and an acyl group such as acetyl, benzoyl, methoxycarbonyl, methoxythiocarbonyl and methylaminocarbonyl etc.

Particularly preferable groups of the (1–8C) straight-chain and branched alkyl are methyl, ethyl, propyl, isopropyl, butyl, isobutyl, amyl, isoamyl, hexyl, heptyl and octyl. Particularly preferable groups of the cyclic alkyl are cyclopropyl, cyclobutyl, cyclopentyl, and cyclohexyl. Useful alkylene groups in the aryl (1–7C) alkyl and the heteroaryl (1–7C) alkyl are methylene, ethylene, trimethylene, tetramethylene, pentamethylene, hexamethylene and heptamethylene. A particularly preferable aryl is phenyl. Particularly useful heteroaryl groups are pyridyl, pyrimidinyl, furyl and thienyl.

Particularly useful groups of the lower alkyl are methyl, ethyl, propyl, isopropyl, butyl, isobutyl and t-butyl. Particularly preferable groups of the lower alkoxy are methoxy, ethoxy, propyloxy, isopropyloxy and butoxy.

Particularly preferable elements of the halogen are fluorine, chlorine and bromine.

The preferable compound of Formula 1 appears when $R^0$, $R^2$, X, Y, Z and J are as described above and $R^1$ is phenyl.

One of the more specified compound of Formula 1 appears when $R^0$, $R^1$, $R^2$, X, Y, Z, J and L are as follows: $R^0$ is phenyl group (the phenyl group may have 1 to 2 substituent groups selected from the group consisting of a halogen, hydroxyl group or methyl group, independently); $R^1$ is phenyl; $R^2$ is any of methyl, butyl, phenylpropyl, 4-morpholin-1-yl-propyl, 1-(ethoxycarbonyl)propyl, 4-methylpiperazin-1-yl-propyl, 2-oxo-1,2-dihydropyridin-1-yl-propyl and (2-pyridyloxy)propyl; X and Y represent unsubstituted carbon or nitrogen atoms; Z is methylene group; J is methylene group; and L is any of methoxy, hydroxyl and acetyloxy.

The furthermore specified compound of Formula 1 appears when $R^0$ is selected from the group consisting of phenyl, 3-fluorophenyl, 4-fluorophenyl, 3,4-difluoro phenyl, 3,5-difluorophenyl and 3-fluoro-4-hydroxyphenyl; and $R^1$, $R^2$, X, Y, Z and J are as described above.

The preferable compound of Formula 1 includes:
(A) 2-(5-acetyloxymethyl -4-oxo-2-phenyl-3,4-dihydropyrimidin-3-yl)-N-{2,3-dioxo-1-phenylmethyl-6-(2-pyridyloxy)}hexylacetamide (Compound No.1),
(B) 2-(5-hydroxymethyl-4-oxo-2-phenyl-3,4-dihydropyrimidin-3-yl)-N-{2,3-dioxo-1-phenylmethyl-6-(2-pyridyloxy)}hexyl acetamide (Compound No.2),
(C) 2-(5-methoxymethyl-4-oxo-2-phenyl-3,4-dihydropyrimidin-3-yl)-N-{2,3-dioxo-1-phenylmethyl-6-(2-pyridyloxy)}hexyl acetamide (Compound No.3),
(D) 2-(5-ethoxycarbonyl-4-oxo-2-phenyl-3,4-dihydropyrimidin-3-yl)-N-{2,3-dioxo-1-phenylmethyl-6-(2-pyridyloxy)}hexyl acetamide (Compound No.4),
(E) 2-(5-acetylaminomethyl-4-oxo-2-phenyl-3,4-dihydropyrimidin-3-yl)-N-{2,3-dioxo-1-phenylmethyl-6-(2-pyridyloxy)}hexylacetamide, (F) 2-(5-methylsulfonylaminomethyl-4-oxo-2-phenyl-3,4-dihydropyrimidin-3-yl)-N-{2,3-dioxo-1-phenylmethyl-6-(2-pyridyloxy)}hexylacetamide, (G) 2-(5-formylaminomethyl-4-oxo-2-phenyl-3,4-dihydro-pyrimidin-3-yl)-N-{2,3-dioxo-1-phenylmethyl-6-(2-pyridyl-oxy)}hexylacetamide, (H) 2-(4-oxo-2-phenyl-5-phenylmethylaminosulfonylaminomethyl-3,4-dihydropyrimidin-3-yl )-N-{2,3-dioxo-1-phenylmethyl-6-(2-pyridyloxy)}hexylacetamide, (I) 2-(4-oxo-2-phenyl-5-phenylmethylsulfonylaminomethyl-3,4-dihydropyrimidin-3-yl)-N-{2,3-dioxo-1-phenylmethyl-6-(2-pyridyloxy)}hexylacetamide, (J) 2-{4-oxo-2-phenyl-5-(2-pyridyl)methylaminosulfonylaminomethyl-3,4-dihydropyrimidin-3-yl}-N-{2,3-dioxo-1-phenylmethyl-6-(2-pyridyloxy)}hexylacetamide, (K) 2-{5-(2-pyridyl)carbonylaminomethyl-4-oxo-2-phenyl- 3,4-dihydropyrimidin-3-yl}-N-{2,3-dioxo-1-phenylmethyl-6-(2-pyridyloxy)}hexylacetamide, and (L) 2-(4-oxo-2-phenyl-5-phenylmethylaminosulfonylaminomethyl-3,4-dihydropyrimidin-3-yl)-N-{2,3-dioxo-1-phenylmethyl-6-(2-oxo-1,2-dihydropyridin-1-yl)}hexylacetamide.

The protective group for hydroxyl group as described in "Protective Groups in Organic Synthesis($2^{nd}$ Ed.)" by T. W. Green et.al. can be used for Rd. It includes a lower alkyl carbonyl and the other acyl protective group; and a tri(lower alkyl) silyl and the other silyl protective group. The preferable protective group includes acetyl group and t-butyldimethylsilyl group.

The compound of Formula 1 can be produced by using a known step-containing chemical techniques for producing the structurally analogous heterocyclic compounds or peptide compounds. For example, as shown in Scheme 1, the objective compound of Formula 1 can be obtained by condensing the compound of Formula 3 with the compound of Formula 4 to give the compound of Formula 2, which is then subject to the removal of the Rd as a protective group, the oxidation, and the deprotection of amino groups or hydroxyl groups if necessary.

Scheme 1

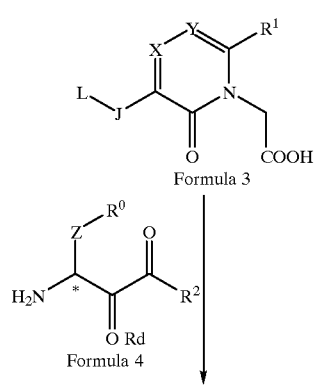

Formula 3

Formula 4

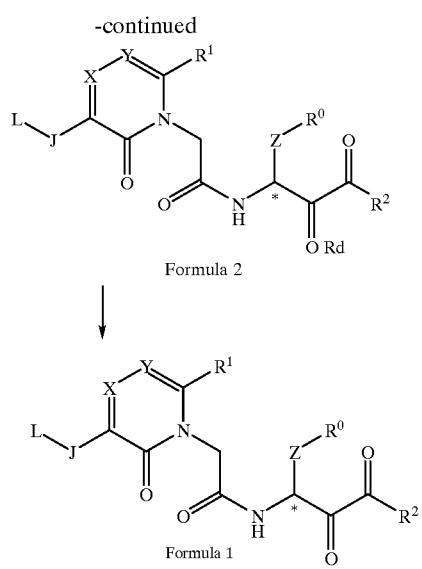

Formula 2

Formula 1

Various methods generally used for the reaction of a carboxylic acid with an amine compound to give their amide compound can be applied to the condensation of the compound of Formula 3 with the compound of Formula 4. For example, a carboxylic acid represented by Formula 3 or its reactive derivative and an amine of Formula 4 are protected at their functional groups not concerned with the reaction according to as necessary and then condensed in an inert solvent at −20° C. to boiling point of the solvent, preferably −10° C. to 60° C., more preferably 0° C.–40° C., or generally at the room temperature. The reactive derivative includes the acid chloride and the carbodiimide derivatives of the carboxylic acid. It may be formed within the reaction system; and, for a preferable example, a carboxylic acid of Formula 3 is used with a base such as 1-hydroxybenzotriazole and a carbodiimide such as 1-(3-dimethylaminopropyl)-3-ethyl-carbodiimide to give the activated derivative of ester, which is condensed with an amine of Formula 4. The compound of Formula 4 may be reacted with the compound of Formula 3 in the equimolar ratio; but the amine of Formula 4 may be used in the range of 0.2–4 mol, preferably 0.5–2 mol relative to 1 mol of a carboxylic acid of Formula 3. The inert solvent is not limited to a specific type; and a polar solvent such as dimethylformamide and tetrahydrofuran is preferable and may be used alone or in combination of two and more.

The preferable compound of Formula 3 includes 5-hydroxymethyl-4-oxo-2-phenyl-3,4-dihydro-3-pyrimidinyl acetic acid(corresponding to the Formula 5, wherein X is carbon, Y is nitrogen, J is methylene group, L is hydroxymethyl and $R^1$ is phenyl group), 5-acethyloxymethyl-4-oxo-2-phenyl-3,4-dihydro-3-pyrimidinyl acetic acid(corresponding to the Formula 5, wherein X is carbon, Y is nitrogen, J is methylene group, L is acetyloxymethyl and $R^1$ is phenyl group), and 5-methoxymethyl-4-oxo-2-phenyl-3,4-dihydro-3-pyrimidinyl acetic acid(corresponding to the Formula 5, wherein X is carbon, Y is nitrogen, J is methylene group, L is methoxymethyl and $R^1$ is phenyl).

The preferable compound of Formula 4 includes 2-amino-7-(1,2-dihydro-2-oxopyridine-1-yl)-3-hydroxy-4-oxo-1-phenylheptane and 2-amino-3-hydroxy-4-oxo-1-phenyl-7-(2-pyridyloxy)heptane.

As is evident to those skilled in the art, the starting materials can be synthesized in various synthetic routes.

For example, the compound of Formula 4 or salt thereof can be easily obtained by conventionally deprotection reaction of the protected amino groups in the ketone derivative of the corresponding oxazolidine and ring-opening reaction of the oxazolidine. The ketone derivative of said oxazolidine can be synthesized as shown in the following steps (1) to (4):

(1) According to the method reported by R. Nishizawa et al. in J. Med. Chem., 20(4), 510–515, 3-amino-2-hydroxy-4-substituted or unsubstituted phenyl butyric acid can be easily synthesized by using an amino acid as the starting material.

The amino acid used as the starting material may be a commercial product, e.g. substituted or unsubstituted phenylalanine. A desired amino acid, if not commercially available, can be obtained by a conventional amino acid synthesis reaction; for example, a substituted phenylalanine with the substituent group introduced on the aromatic ring can be obtained by condensing an available acetamide malonic acid ester with a substituted benzyl halide to give the ester, and then by hydrolysis of the ester and successive by decarboxylation reaction of the resultant compound and deprotection reaction of the amino group of the compound thus obtained.

(2) The 3-amino group of the 3-amino-2-hydroxy-4-substituted or unsubstituted phenylbutyric acid thus obtained is protected with a suitable protective group such as t-butyloxycarbonyl group and then the resulting compound is conventionally condensed with N,O-dimethylhydroxylamine or a salt thereof to derive 3-N-protected amino-2-hydroxy-4-substituted or unsubstituted phenylbutyric acid-N,O-dimethylhydroxylamide.

(3) The amide thus obtained can be conventionally treated in 2,2-dimethoxypropane with a catalytic amount of p-toluenesulfonic acid to give easily 3-N-protected-5-(N-methoxy-N-methyl)carbamoyl-2,2-dimethyl-4-substituted or unsubstituted phenylmethyloxazolidine.

(4) The amide thus obtained, which is known an activated amide as is apparent to those skilled in the art, can be easily converted to the ketone derivative by the below treatment: for example, according to a method disclosed in Japanese Laid-Open Patent Publication No. 143517/1996, the oxazolidine can be treated with a Grignard reagent corresponding to group $R^2$ in a solvent such as tetrahydrofuran under the atmosphere of inert gas such as argon to substitute the N,O-dimethylhydroxylamino group with the group $R^2$, so that the ketone derivative of the oxazolidine having the group $R^2$ introduced into it can be synthesized.

The compound of Formula 3 (X is carbon and Y is nitrogen) as an intermediate, can be synthesized by a available route as described below: the compound of Formula 5(X is carbon, Y is nitrogen, J is carbonyl group, L is ethoxy group or hydroxyl group), which can be obtained by the method disclosed in Japanese Laid-Open Patent Publication No. 286946/1993 filed by IMPERIAL CHEMICAL INDUSTRIES PLC, can be used for a key intermediate to derive various compounds of Formula 3 which has the different combination of J and L through their respective routes as shown by the following methods (1)–(4)in Scheme 2.

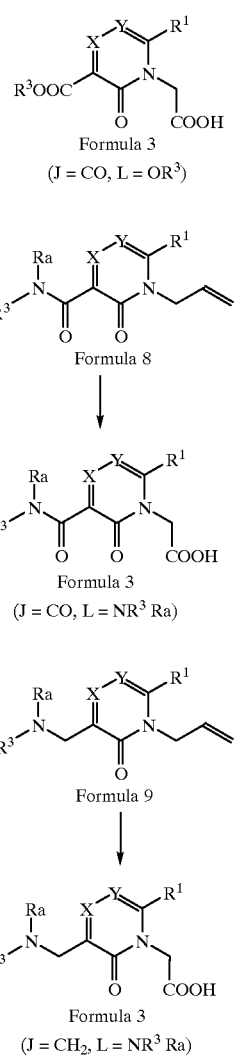

Scheme 2

(1) The compound of J=methylene group and L=$OR^3$ in the Formula 3:

The compound of Formula 5 wherein J is carbonyl group and L is hydroxyl group can be conventionally treated with a reagent such as oxalyl chloride to derive the acid chloride, which is then reduced with an appropriate reducing agent such as lithium tri-t-butoxy aluminium hydride in an inert solvent such as tetrahydrofurane under the atmosphere of inert gas such as argon to derive the compound of Formula 6(J=methylene group, L=hydroxyl group in the Formula 5). The hydroxyl group of the compound of Formula 6 is protected, as the occasion demands, to derive the compound of Formula 7 (J=methylene group, L=$OR^3$ in the Formula 5), and the resultant olefine is then oxidized to cleavage directly with ruthenium tetraoxide or indirectly with osmium tetraoxide through the 1,2-diol to obtain the compound of Formula 3 wherein J is methylene group and L is $OR^3$.

(2) The compound of J=carbonyl group and L=$OR^3$ in the Formula 3:

Through the route 2, the acid chloride of the compound of Formula 5 as shown in the above (1) can be treated with an alcohol represented by $R^3OH$ in an inert solvent such as methylene chloride and tetrahydrofuran under the presence of a base such as 4-dimethylaminopyridine, as the occasion demands, to derive the compound of Formula 5 wherein J is carbonyl group and L is $OR^3$, and the resultant olefine is then oxidized to cleavage and to obtain the compound of Formula 3 wherein J is carbonyl group and L is $OR^3$.

(3) The compound of J=carbonyl group and $L=NR^3R_a$ in Formula 3:

Through the route 3, the acid chloride of the compound of Formula 5 as shown in the above (1) can be treated with an amine represented by $R^3R_aNH$ in the same way as described in the above (2) to derive the compound of Formula 8 (J=carbonyl group; $L=OR^3$ in the Formula 5) wherein J is carbonyl group and L is $NR^3R_a$, whose olefine is then oxidized to cleavage and to obtain the compound of Formula 3 wherein J=carbonyl group; $L=NR^3R_a$.

(4) The compound of Formula 3 wherein J=methylene group; $L=NR^3R_a$:

Through the route 4, the compound of Formula 7 (J=methylene group, $L=OR^3$ in the Formula 5), which can be synthesized by the method as described in the above (1) and has the leaving group such as sulfonyl group for $R^3$, can be conventionally treated with an additive such as sodium iodide in an inert solvent such as methylene chloride under the atmosphere of inert gas such as argon to convert the $L=OR^3$ into L=halogen, and then treated with an amine represented by $R^3R_aNH$ under the presence of an amine such as triethylamine if necessary to derive the compound of Formula 9 (J=methylene group; $L=NR^3R_a$ in the Formula 5), and the resultant olefine is then oxidized to cleavage and to obtain the compound of Formula 3 wherein J is methylene group and L is $NR^3R_a$.

The compound of Formula 3 wherein X is nitrogen and Y is carbon as an intermediate, can be obtained, according to a available pathway, by synthesizing the compound of Formula 5 wherein X is nitrogen and Y is carbon through the route as shown in the scheme 3, and then treating the synthesized compound in the similar way as described in the above (1) according to the scheme 2.

A process for producing the compound of Formula 5 wherein X is nitrogen and Y is carbon will be described below by the scheme 3 where BOC and CBZ represent t-butyloxycarbonyl group and benzyloxycarbonyl group respectively.

Scheme 3

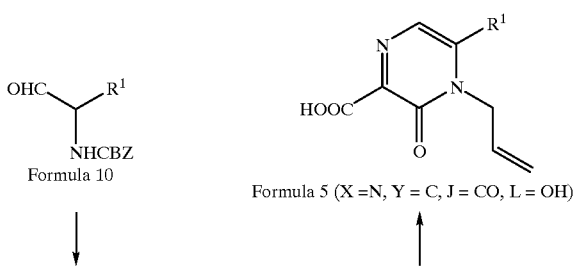

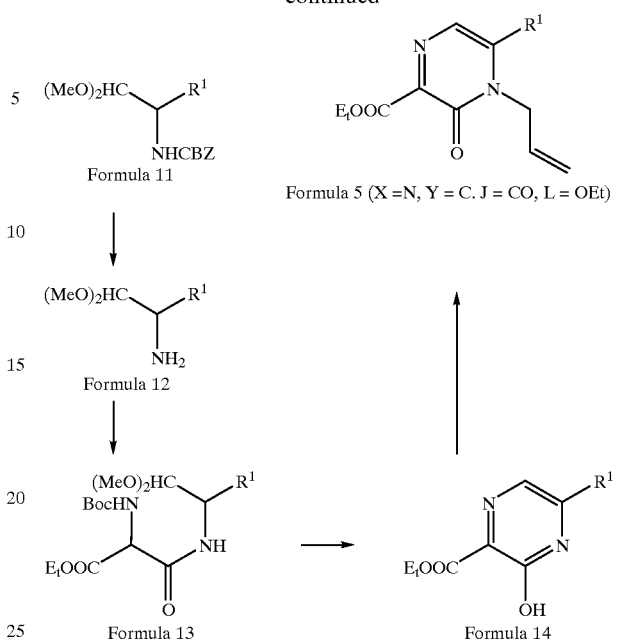

The aldehyde represented by Formula 10 can be easily synthesized by the synthetic method reported by D. H. Rich et al. in J. Org. Chem. 43(18), 3624–3626 (1978). The aldehyde is treated with a suitable alcohol (methanol in this case) under the presence of an acid catalyst to derive the compound represented by Formula 11, whose benzyloxy-carboxyl group is conventionally hydrogenolyzed to convert into the compound represented by Formula 12. The amine of Formula 12 can be conventionally condensed with t-butyloxycarbonylaminomalonic acid monoester to obtain the compound of Formula 13.

The compound of Formula 13 can be ring-closed by using the synthetic method reported by H. Taguchi et al. in Peptide Chemistry, 169–172 (1994) to convert into the compound represented by Formula 14. The compound of Formula 14 is treated with a suitable base under the presence of an alkylating agent to obtain the compound of Formula 5 wherein X is nitrogen, Y is carbon, J is carbonyl group and L is ethoxy group. The carboxyl-protecting group of the compound thus obtained can be conventionally removed to derive easily the compound of Formula 5 wherein X is nitrogen, Y is carbon, J is carbonyl group and L is hydroxyl group as a key intermediate.

The compound of Formula 3 wherein both X and Y are nitrogen as an intermediate, can be obtained according to a available pathway by synthesizing the compound of Formula 5 wherein both X and Y are nitrogen through the route as shown in the scheme 4, and then treating the synthesized compound in the similar way as described in the above (1) according to the scheme 2.

A process for producing the compound of Formula 5 wherein both X and Y are nitrogen will be described below.

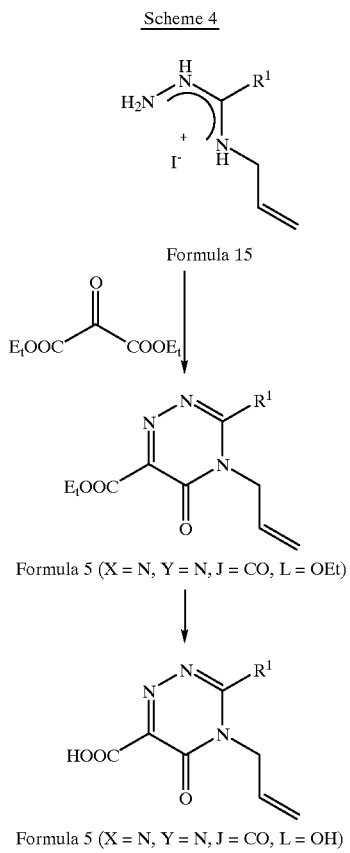

Scheme 4

Formula 15

Formula 5 (X = N, Y = N, J = CO, L = OEt)

Formula 5 (X = N, Y = N, J = CO, L = OH)

The amidolazone represented by Formula 15 can be synthesized by using the synthetic method reported by H. J. Metz and H. Neunhoeffer in Chem. Ber. 115, 2807–2818 (1982). The amidolazone, without isolation and purification, can be reacted with diethylketomalonate under the presence of a suitable base for cyclizing to derive the compound of Formula 5 wherein X and Y is nitrogen respectively, J is carbonyl group and L is ethoxy group. The carboxyl-protecting group of the compound thus obtained can be conventionally hydrolyzed to convert the compound of Formula 3 wherein X and Y is nitrogen respectively, J is carbonyl group and L is hydroxyl group.

The present invention includes the above intermediates and their synthesizing processes used for producing the compound of Formula 1.

The compound of Formula 1 can be synthesized by the processes as described in the below (A)–(I). The intermediates having the same groups also can be produced by the analogous methods, as will be described later. The symbols and the groups used here have their respective same meanings as described above.

(A) A synthesis by oxidizing the alcohol represented by Formula 2:

An unprotected L group, if it is unstable under an oxidation condition, is preferably or necessarily protected in advance of the oxidation by substituting hydrogen atom of its amino group or hydroxyl group with an appropriate $R^3$ (excluding hydrogen) or $R_a$(excluding hydrogen) which is then removed after oxidation. The simple method for oxidation is to use excess dimethylsulfoxide and water-soluble carbodiimide under the presence of pyridinium trifluoroacetate for a catalyst, for example, in an inert solvent such as methylene chloride around the room temperature, as shown in Example 2(7) mentioned later. The oxidation may be conducted by using oxalyl chloride, dimethylsulfoxide and a tertiary amine or by using pyridinium chlorochromate in methylene chloride.

(B) A synthesis of the compound of Formula 1 having a free amino group, which comprises removing an amino-protecting group from the amino-protected compound of the Formula 1: (for example, for a synthesis of the Formula 1 wherein any one of $R^3$ and $R_a$ is hydrogen and the other is an alkyl group, any one of $R^3$ and $R_a$ is substituted with an amino-protecting group such as t-butoxycarbonyl group for the purpose of protection and activation of a primary amino group, and then the introduced amino-protecting group is removed.)

Any conventional method for removing an amino-protecting group can be used provided that it gives no cleavage to the amide bonds in the compound of Formula 1. It includes removal of an amino-protecting group by treatment with a strong acid such as hydrogen chloride in an inert solvent such as 1,4-dioxane, or removal of an amino-protecting group by heating treatment in the coexistence of p-toluenesulfonic acid in methanol.

(C) A synthesis of the compound of Formula 1 wherein $R^3$ is an acyl group:

This compound can be obtained conventionally by acylating the amino group or the hydroxyl group of compound of Formula 1 wherein $R^3$ is hydrogen. A simple acylation method is to use an acid halide corresponding to the acyl group in an inert solvent such as tetrahydrofuran. Another useful method is to use a coupling agent for condensation reaction with a corresponding carboxylic acid. The coupling agent includes carbodiimides such as 1-(3-dimethyl aminopropyl)-3-ethylcarbodiimide. 1-hydroxybenzotriazole may be added for an auxiliary to the condensation reaction.

(D) The compound of Formula 1 wherein $R^1$ or $R^2$ has $COOR_a$ or $CONR_bR_c$, or $R^2$ is $COOR_a$ or $CONR_bR_c$ can be obtained by reacting(acylating) the compound of Formula 1 wherein $R^1$ or $R^2$ has COOH (or its reactive group) or $R^2$ is COOH(or its reactive group) with a compound having $HOR_a$ or $HNR_bR_c$ corresponding to $R_a$ or $R_bR_c$.

(E) The compound of Formula 1 wherein $R^3$ is sulfonyl group can be obtained by sulfonylating(sulfonylation reaction) the compound of Formula 1 having the primary amino group wherein $R^3$ is hydrogen with a corresponding sulfonyl chloride to said sulfonyl group. This reaction can be carried out at room temperature or under cooling on ice under the presence of a tertiary amine in an inert solvent such as tetrahydrofuran. If the desired sulfonyl chloride is not commercially available, it may be synthesized to use by a known method.

(F) The compound of Formula 1 wherein $R^3$ is $R_a$ excluding hydrogen can be obtained by reacting (substituting) the compound of Formula 1 having the amine group or the hydroxyl group wherein $R^3$ is hydrogen with a compound represented by $R_a$-M having an usual leaving group M such as halogen, methylsulfonyloxy group and trifluoromethyl-sulfonyloxy group.

(G) The Formula (1) compound wherein at least one of $R^1$, $R^2$ and L is an aryl group or a heteroaryl group whose ring has hydroxyl group as a substituent group can be obtained by cleaving (cleavage reaction) the corresponding alkyl ether or acyloxy ester bond of the compound of Formula 1 wherein at least one of $R^1$, $R^2$ and L is an aryl group or a heteroaryl group whose ring has a lower alkoxy substituent group or a lower acyloxy substituent group. The simple method includes hydrolysis of the acyloxy group under an acidic or alkaline condition.

(H) The compound of Formula 1 wherein $R^1$ or $R^2$ has a substituted carboxylic group, or $R^2$ is carboxylic group ($R_a$ in the group $COOR_a$ is hydrogen) can be obtained by removing the ester group from a corresponding ester compound which is a compound which said carboxyl group is protected. This reaction includes hydrolysis with an alkali such as sodium hydroxide, hydrogenolysis in the case of benzyl ester, and decomposition of t-butyl ester under an acid condition.

(I) The compound of Formula 1 wherein $R^3$ in L is $R_bR_cNCO$ or $R_bR_cNCS$, and $R_c$ is hydrogen can be obtained by reacting(acylating) the compound of Formula 1 having the amino group or the hydroxyl group with the corresponding isocyanate or thioisocyanate represented by $R_bNCO$ or $R_bNCS$.

The alcohol compound of the Formula 2 used for a material of the above (A) can be obtained by condensing the compound of Formula 3 with the compound of Formula 4 as mentioned above. The above (A), (B), (C), (D), (E), (F), (G), (H) and (I), which are the processes for producing the compound of Formula 1, can be similarly applied for producing analogous intermediate compounds having the same groups in Formula 2 or 3.

A protective group is desirably in some cases used for all the synthetic steps described above. The protective group can be removed at the stage after the final product or the target compound is synthesized.

As is evident to those skilled in the art, a series of processes leading from the starting material through the intermediates to the final product of the present invention may be modified by suitable consideration on a method for condensing or removing a protective group etc.

A pharmacologically acceptable salt of the compound of Formula 1 includes: when the compound of Formula 1 is an acidic one, the alkali metal salt, the alkaline earth metal salt, the aluminum salt, the ammonium salt or the salt obtained by reacting with an organic base(such as N-methylpiperazine and morpholine) giving the pharmaceutically acceptable cation; when the compound of Formula 1 is a basic one, the acid-addition salt obtained by reacting with an acid(such as, sulfuric acid, formic acid and acetic acid) giving the pharmacologically acceptable anion.

The present compound used for a chymase inhibitor is administered orally or parenterally alone or with excipients or carriers in a pharmaceutical composition such as injection, inhalant, tablet, granule, subtle granule, powder, capsule, suppository, eye drop, paste, ointment and spray. As excipient or carrier, a pharmaceutically acceptable additive is selected; and the type and composition is determined according to the route and method of administration. For example, an injection contains preferably sodium chloride or saccharide such as glucose and mannitol. An oral preparation contains preferably starch, lactose, crystalline cellulose and magnesium stearate.

The content of the present compound in the pharmaceutical composition varies depending on the preparation form, but is usually in the range of 0.1 to 100% by weight, preferably 1 to 98% by weight. For example, an injection usually contains the active ingredient in the range of 0.1 to 30% by weight, preferably 1 to 10% by weight. The present compound is used with additives in an oral preparation form such as tablet, capsule, powder, granule, liquid and dry syrup. The capsule, tablet, granule and powder generally contain 5 to 100% by weight, preferably 25 to 98% by weight, of the active ingredient.

Although the dosage is determined depending on the age, weight and symptom of a patient and an object of therapy, the therapeutic amount is usually 1 to 100 mg/kg/day for parenteral administration and 5 to 500 mg/kg/day for oral administration.

The present compound is characterized in that it is low toxic and, even if successively administered, causes little toxicity accumulation. For example, the present compound, even if orally administered into a hamster at a dosage of 100 mg/kg twice a day for 3 weeks, was observed to give no symptom of toxicity.

EXAMPLE

The present invention will be described in more details with reference to the Examples as shown below, but shall not be limited to these examples.

The examples, unless otherwise noted, used the following operations.

(1) The solvent was removed to concentrate under a reduced pressure of 5 to 20 mmHg in a rotary evaporator on a water bath at a temperature of 50° C. or less;

(2) Silica gel chromatography was conducted using BW-820 MH (Fuji Silicia); preparative thin layer chromatography used a TLC plate having a thickness of 0.25 or 0.5 mm as necessary (silica gel 60F254, 20×20 cm) (Merck); the elution solvent/developing solvent ratio was indicated by volume/volume;

(3) The melting point was not corrected, and (dec) indicates decomposition. The sample synthesized by the method described in an Example was measured to show the melting point described there; however, even a substance synthesized by the same method, if it has crystal polymorphism, may show a different melting point;

(4) The final product gave a satisfactory nuclear magnetic resonance (NMR) spectrum;

For NMR, Gemini-200 (200 MHz) made by Varian was used and it is shown in ppm with tetramethylsilane (TMS) used for an internal standard substance; customary abbreviations were used for representing the shapes of detected signals;

(5) Mass spectrum was measured using VG Auto Spec (VG Co., Ltd.) by the EI method or the FAB method;

(6) Infrared (IR) absorption spectrum was measured by IR spectrophotometer A-202 (Nippon Bunko Co., Ltd.) using a polystyrene film for a standard substance;

(7) In general, TLC was used for monitoring the reaction; the described reaction time is merely illustrative and does not necessarily provide an optimum time;

(8) The described yield is for explanation and does not necessarily equal what an optimum method may provide; a synthesis was repeatedly conducted to obtain a large amount of substance if necessary.

Example 1

Synthesis of 2-amino-3-hydroxy-4-oxo-1-phenyl-7-(2-pyridyloxy)heptane 2(p-toluenesulfonic acid)salt used for an intermediate was conducted through the below steps:
(1)(4S,5R)-3-t-butyloxycarbonyl-2,2-dimethyl-5-{3-(1-oxo)butenyl}-4-phenylmethyloxazolidine:
(4S,5R)-3-t-butyloxycarbonyl-5-(N-methoxy-N-methyl)carbamoyl -2,2-dimethyl-4-phenylmethyloxazolidine (37.85 g, 100 mmol) was dissolved in diethylether(100 ml) and tetrahydrofurane(20 ml) under the atmosphere of nitrogen gas. To this solution was a 1M diethylether solution(120 ml) of allyl-magnesium bromide (120 mmol) added dropwise at −15° C., and then the solution was turned up to the room temperature. After 30 min, to the reaction solution was a saturated ammonium chloride solution added and then the solution was extracted with ethyl acetate. The organic layer was washed with an aqueous saturated sodium chloride solution, dried over anhydrous sodium sulfate, and concentrated under a reduced pressure to give a residue, which was purified by silicagel column chromatography (silicagel 200 g, hexane/ethyl acetate=14/1) to obtain the object compound (14.44 g, yield 40%).

1H-NMR (CDCl$_3$); 1.53 (15H, s), 2.75–3.35 (4H, complex), 4.25 (1H, br. s), 4.43 (1H, br. s), 5.00 (1H, br. d, J=18.1 Hz), 5.12 (1H, dd, J=1.3, 10.2 Hz), 5.80 (1H, m), 7.16–7.36 (5H, complex).

(2)(4S,5R)-3-t-butyloxycarbonyl-2,2-dimethyl-5-{3-(1-hydroxy)butenyl}-4-phenylmethyloxazolidine:

To ether(100 ml) previously cooled to −10° C. was lithium aluminium hydride(610 mg, 16.1 mmol) added under the atmosphere of nitrogen gas, and the solution was cooled down to −72° C. To the solution was a diethyl ether(100 ml) solution of the (4S,5R)-3-t-butyloxycarbonyl-2,2-dimethyl-5-{3-(1-oxo) butenyl}-4-phenylmethyloxazolidine (14.44 g, 40.2 mmol)added dropwise f or 30 min. After 20 min, to the solution was a saturated ammonium chloride solution(50 ml)added dropwise and then the solution was turned up to the room temperature. To the solution was a saturated ammonium chloride solution and ethyl acetate added to extract. The organic layer was washed with an aqueous saturated sodium chloride solution, dried over anhydrous sodium sulfate, and concentrated under a reduced pressure to obtain the object compound(14.49 g, yield 100%).

MS; m/z=362 (M+1)

(3)(4S,5R)-3-t-butyloxycarbonyl-2,2-dimethyl-4-phenylmethyl-5-{3-(1-phenylmethyloxy)butenyl} oxazolidine:

To a solution of (4S,5R)-3-t-butyloxycarbonyl-2,2-dimethyl-5-{3-(1-hydroxy)butenyl}-4-phenylmethyloxazolidine (14.49 g, 40.1 mmol)dissolved in tetrahydrofuran(200 ml) were benzylbromide (5.8 ml, 48.1 mmol) and sodium hydride(1.92 g, 48.1 mmol)added under the atmosphere of nitrogen gas, and then the solution was heated under reflux. After 7 hrs, the solution was set free from heating, and then left to stand, diluted with ethyl acetate, and washed with distilled water and an saturated aqueous sodium chloride solution successively. The organic layer was dried over anhydrous sodium sulfate, and then concentrated under a reduced pressure to give a residue, which was purified by silicagel column chromatography (silicagel 200 g, hexane/ethyl acetate=14/1) to obtain the object compound (17.11 g, yield 95%).

MS; m/z=452 (M+1)

(4)(4S,5R)-3-t-butyloxycarbonyl-2,2-dimethyl-4-phenylmethyl-5-(4-hydroxy-1-phenylmethyloxy)butyloxazolidine:

(4S,5R)-3-t-butyloxycarbonyl-2,2-dimethyl-4-phenylmethyl-5-{3-(1-phenylmethyloxy)butenyl}oxazolidine (17.11 g, 37.9 mmol) was dissolved intetrahydrofurane(76 ml)and cooled on ice under the atmosphere of nitrogen gas. To the solution was a 0.5M tetrahydrofuran solution(164 ml) of 9-BBN (82 mmol) added dropwise, and then the solution was stirred at the room temperature overnight. To the reaction solution cooled on ice were methanol(5 ml), 6N aqueous sodium hydroxide solution(30 ml)and 30% aqueous hydrogen peroxide solution(60 ml)added dropwise successively. The solution was filtered to remove a precipitated solid and diluted with ethyl acetate to separate a water layer. The organic layer was washed with 10% aqueous sodium thiosulfate solution and a saturated sodium chloride aqueous solution successively, dried over anhydrous sodium sulfate, and concentrated under a reduced pressure to give a residue, which was purified by silicagel column chromatography (silicagel 300 g, hexane/ethyl acetate=5/1-1/1) to obtain the object compound (15.2 g, yield 85%).

1H-NMR (CDCl$_3$); 1.35–1.67 (19H, complex), 2.65–2.95 (1H, br. m), 3.13–3.54 (4H, complex), 3.97–4.14 (2H, complex), 4.54 (2H, br. s), 7.10–7.34 (10H, overlapped with solvent peak): MS; m/z=470 (M+1)

(5)(4S,5R)-3-t-butyloxycarbonyl-2,2-dimethyl-4-phenylmethyl-5-{1-phenylmethyloxy-4-(2-pyridyloxy)}butyloxazolidine:

To a solution of (4S,5R)-3-t-butyloxycarbonyl-2,2-dimethyl-4-phenylmethyl-5-(4-hydroxy-1-phenylmethyloxy) butyloxazolidine (36.84 g, 78.4 mmol ) dissolved in tetrahydrofurane (390 ml ) were 2-bromopyridine (7.9 ml, 82.4 mmol) and potassium t-butoxide (11.1 g, 94.1 mmol) added under the atmosphere of argon gas, and then the solution was heated under reflux. After 1.5 hrs, the solution was set free from heating, and then left to stand, diluted with ethyl acetate, and washed with distilled water and an saturated aqueous sodium chloride solution successively. The organic layer was dried over anhydrous sodium sulfate and concentrated under a reduced pressure to give a residue, which was purified by silicagel column chromatography (silicagel 350 g, hexane/ethylacetate=9/1) to obtain the object compound (42.13 g, yield 98%).

1H-NMR (CDCl$_3$); 1.34–1.80 (19H, complex), 2.65–2.98 (1H, br. m), 3.10–3.41 (2H, complex), 3.93–4.23 (4H, complex), 4.51 (2H, br. s), 6.68 (1H, d, J=8.4 Hz), 6.80–6.89 (1H, m), 7.07–7.33 (10H, overlapped with solvent peak), 7.50–7.60 (1H, m) 8.11–8.16 (1H, m): MS; m/z=547 (M+1).

(6)(4S,5R)-3-t-butyloxycarbonyl-2,2-dimethyl-4-phenylmethyl-5-{1-hydroxy-4-(2-pyridyloxy)}butyl-oxazolidine:

To a solution of (4S,5R)- 3-t-butyloxycarbonyl-2,2-dimethyl-4-phenylmethyl-5-{1-phenylmethyloxy-4-(2-pyridyloxy)}butyloxazolidine(42.13 g, 77.1 mmol) dissolved in ethanol/cyclohexene(2/1, 770 ml) was 20% palladium hydroxide on carbon (4.2 g, 10% by weight) added under the atmosphere of argon gas, and then the solution was heated under reflux. After 2.5 hrs, the solution was set free from heating, and then left to stand, and filtered to remove the catalyst. The filtrate was concentrated under a reduced pressure to give a residue, which was purified by silicagel column chromatography (silicagel 280 g, hexane/ethyl acetate/methanol=50/10/1) to obtain the object compound (30.46 g, yield 87%).

1H-NMR (CDCl$_3$); 1.01–1.81 (17H, complex), 2.40 (1H, d, J=4.4 Hz), 2.67–2.85 (1H, br. m), 3.13–3.34 (2H, complex) 3.75 (1H, dd, J=3.8, 6.6 Hz) 3.81–4.32 (4H, complex) 6.69 (1H, d, J=8.4 Hz), 6.80–6.89 (1 H, m), 7.09–7.33 (5H, complex), 7.51–7.61 (1H, m), 8.11–8.16 (1H, br. dd, J=1.7, 50 Hz)

(7)(4S)-3-t-butyloxycarbonyl-2,2-dimethyl-4-phenylmethyl-5-{1-oxo-4-(2-pyridyloxy) }butyloxazolidine:

To a solution of (4S)-3-t-butyloxycarbonyl-2,2-dimethyl-4-phenylmethyl-5-{1-hydroxy-4-(2-pyridyloxy)}butyl oxazolidine(16.20 g, 35.5 mmol)dissolved in methylene chloride (180 ml) were pyridine(1.4 ml, 17.7 mmol) and dimethylsulfoxide (12.6 g, 177 mmol)added dropwise under the atmosphere of nitrogen gas, and the solution was cooled on ice. To the solution was trifluoroacetic acid(4.1 ml, 53.2 mmol) added dropwise and then 1-(3-dimethylaminopropyl)-3-ethylcarbodiimidehydrochloride (20.8 g, 106 mmol) added, and the solution was turned up to the room temperature. After 1 hr, the reaction solution was washed with distilled water and an aqueous saturated sodium bicarbonate solution successively. The organic layer was dried over anhydrous sodium sulfate and concentrated under a reduced pressure to give a residue, which was purified by silicagel column chromatography (silicagel 160 g, hexane/ethyl acetate/methanol=50/10/1) to obtain the object compound (15.58 g, yield 97%). The compound was left to stand to crystallize.

1H-NMR (CDCl$_3$); 1.09–1.80 (15H, complex), 1.88–2.09 (2H, m), 2.38–3.34 (4H, complex), 4.14–4.34 (3H, complex), 4.34–4.57 (1H, m), 6.53–6.72 (1H, m), 6.77–6.93 (1H, m) 7.11–7.38 (5H, complex), 7.54–7.62 (1H, m), 8.04–8.16 (1H, m).

(8) 2-amino-3-hydroxy-4-oxo-1-phenyl-7-(2-pyridyloxy) heptane 2(p-toluenesulfonic acid)salt:

To a solution of (4S)-3-t-butyloxycarbonyl-2,2-dimethyl-4-phenylmethyl-5-{1-oxo-4-(2-pyridyloxy)}butyl oxazolidine (13.63 g, 30.0 mmol) dissolved in ethanol(60 ml) was p-toluenesulfonic acid monohydrate(11.4 g, 60.0 mmol) added, and then the solution was heated under reflux for 2 hrs. The reaction solution was then concentrated under a reduced pressure to obtain the object compound(21.7 g, quantitative yield). The concentrated residue obtained in this step of the Example was passed directly to the next Example without further purification.

MS; m/z=315 (M+1)

Example 2

Synthesis of 2-(5-acetyloxymethyl-4-oxo-2-phenyl-3,4-dihydropyrimidine-3-yl)-N-{2,3-dioxo-1-phenylmethyl-6-(2-pyridyloxy)}hexylacetoamide(Compound No.1) was conducted through the below steps:

(1) 3-allyl-5-hydroxymethyl-2-phenyl-3,4-dihydropyrimidine-4-one:

To a solution of 3-allyl-2-phenyl-3,4-dihydro pyrimidin-4-on-5-carboxylic acid(10.0 g, 39 mmol)dissolved in methylene chloride(78 ml) were dimethylformamide (0.03 ml, 0.39 mmol) and oxalyl chloride(7.48 ml, 78 mmol) added, and the solution was stirred at the room temperature for 2.5 hrs. The reaction solution was concentrated under a reduced pressure to give a crystalline residue, which was dried, suspended in diglyme and cooled to −78° C. under the atmosphere of argon gas. To the suspension was a diglyme solution of lithium tri-t-butoxy aluminium hydride (29.75 g, 117 mmol)added, and the solution was stirred for 3 hrs, then turned up to the room temperature. The reaction solution was diluted with ethyl acetate, washed with a mixed solution of concentrated hydrochloric acid and an aqueous saturated sodium chloride, and then washed with an aqueous saturated sodium chloride. The organic layer was dried over anhydrous sodium sulfate and concentrated under a reduced pressure to give a residue, which was dissolved in tetrahydrofurane(200 ml)and cooled on ice under the atmosphere of argon gas. To the solution was lithium tri-t-butoxy aluminium hydride(9.91 g, 39 mmol)added. The solution was stirred for 30 min, diluted with ethyl acetate and washed with an aqueous 2N hydrochloric acid solution and a saturated sodium chloride aqueous solution successively. The organic layer was dried over anhydrous sodium sulfate and concentrated under a reduced pressure to give a residue, which was purified by crystallization from ethyl acetate/methanol/hexane to obtain the object compound (5.03 g, yields 63%).

1H-NMR (CDCl$_3$); 4.56 (2H, m), 4.62 (2H, s), 4.55 (1H, br. d, J=17.2 Hz) 5.22 (1H, br. d, J=10.5 Hz), 5.78–5.98 (1H, m), 7.49 (5H, complex), 7.99 (1H, s): MS; m/z=243 (M+1)

(2) 5-acetyloxymethyl-3-allyl -2-phenyl-3,4-dihydropyrimidine-4-one:

To a solution of 3-allyl-5-hydroxymethyl-2-phenyl-3,4-dihydropyrimidine-4-one (1.0 g, 4.13 mmol) dissolved in pyridine(4.1 ml)were acetic anhydride(0.78 ml, 8.12 mmol) and a catalytic amount of 4-dimethylaminopyridine added, and then the solution was stirred for 3 hrs. The reaction solution was diluted with ethyl acetate and washed with distilled water and a saturated sodium chloride aqueous solution successively. The organic layer was dried over anhydrous sodium sulfate and concentrated under a reduced pressure to give a residue, which was purified by silicagel column chromatography (silicagel 40 g, hexane/ethyl acetate=1/1) to obtain the object compound (791 mg, yield 67%).

1H-NMR (CDCl$_3$); 2.14 (3H, s), 4.56 (2H, br. dt, J=1.5, 5.4 Hz) 4.95 (1H, br. d, J=17.2 Hz), 5.09 (2H, s), 5.20 (1H, br. d, J=10.3 Hz), 5.78–5.98 (1H, m), 7.49 (5H, complex), 8.05 (1H, s): MS; m/z=285 (M+1).

(3) 5-acetyloxymethyl-2-phenyl-3-(2,3-dihydroxy)propyl-3,4-dihydropyrimidine-4-one:

To a solution of 5-acetyloxymethyl-3-allyl-2-phenyl-3,4-dihydropyrimidine-4-one(791 mg, 2.76 mmol)dissolved in tetrahydrofuran(10 ml) were 4-methylmorpholine-N-oxide (50% by weight aqueous solution 1.3 ml, 5.52 mmol)and osmium tetroxide(4% aqueous solution 1.28 ml, 0.20 mmol) added, and then the solution was stirred at the room temperature overnight. The reaction solution was diluted with ethyl acetate and washed with 10% aqueous sodium thiosulfate solution and a saturated sodium chloride aqueous solution successively. The organic layer was dried over anhydrous sodium sulfate and concentrated under a reduced pressure to give a residue, which was purified by silicagel column chromatography (silicagel 32 g, ethyl acetate/methanol=20/1) to obtain the object compound (580 mg, yield 66%).

1H-NMR (CDCl$_3$); 2.14 (3H, s), 2.48 (1H, br. t, J=6.6 Hz), 3.31–3.60 (3H, complex), 3.81–3.95 (1H, m), 4.10–4.18 (2H, complex), 5.09 (2H, s) 7.42–7.55 (5H, complex), 8.10 (1 H, s): Ms; m/z=319 (M+1).

(4) 5-acetyloxymethyl-2-phenyl-3,4-dihydropyrimidine-4-on-3-yl-acetaldehyde:

To a solution of 5-acetyloxymethyl-2-phenyl-3-(2,3-dihydroxy)propyl-3,4-dihydropyrimidine-4-one(580 mg, 1.82 mmol) dissolved in tetrahydrofurane(9 ml) was an aqueous solution of sodium periodate (468 mg, 2.19 mmol) dissolved in 5.8 ml of water added at the room temperature, and then the solution was stirred for 2 hrs. The reaction solution was diluted with ethyl acetate and washed with distilled water and a saturated sodium chloride aqueous solution successively. The organic layer was dried over anhydrous sodium sulfate and concentrated under a reduced pressure to obtain the object compound (471 mg, yield 90%)as a crystalline residue. 1H-NMR CDCl$_3$); 2.14 (3H, s), 4.76 (2H, s), 5.08 (2H, s), 7.39–7.55 (5H, complex), 8.11 (1H, s), 9.62 (1H, s): MS; m/z=287 (M+1)

(5) 5-acetyloxymethyl-2-phenyl-3,4-dihydropyrimidin-4-on-3-yl-acetic acid:

To a solution of 5-acetyloxymethyl-2-phenyl-3,4-dihydropyrimidin-4-on-3-yl-acetaldehyde (471 mg, 1.64 mmol) dissolved in 2-methyl-2-propanol(8.2 ml) were 2-methyl-2-butene(0.76 ml, 7.22 mmol), an aqueous solution of disodium hydrogenphosphate(233 mg, 1.64 mmol) dissolved in 2.3 ml of water and an aqueous solution of sodium chlorite (519 mg, 5.74 mmol) dissolved in 5.2 ml of water added at the room temperature, and then the solution was stirred over night. The reaction solution was diluted with a mixed solvent of chloroform/2-propanol (3/1) and washed with 20% aqueous citric acid solution. The organic layer was dried over anhydrous sodium sulfate and concentrated under a reduced pressure to obtain the object compound (720 mg, quantitative yield).

1H-NMR {CDCl$_3$+(CD$_3$)$_2$SO}; 2.13 (3H, s), 4.57 (2H, s), 5.07 (2H, s), 7.51 (5H, complex), 8.80 (1H, s): MS; m/z=301 (M−1)

(6) 2-(5-acetyloxymethyl-4-oxo-2-phenyl- 3,4-dihydropyrimidin-3-yl)-N-{2-hydroxy-3-oxo-1-phenylmethyl-6-(2-pyridyloxy)}hexylacetamide:

5-acetyloxymethyl-2-phenyl-3,4-dihydropyrimidine-4-on-3-yl-acetic acid(720 mg, 2.38 mmol) and 2-amino-3-hydroxy-4-oxo-1-phenyl-7-(2-pyridyloxy)heptane 2(p-toluenesulfonic acid)salt(1.66 g, 2.38 mmol) were dissolved in a mixed solvent of dimethylformamide (6 ml) and tetrahydrofuran (6 ml) and cooled on ice. To the solution were 1-hydroxybenzotriazole monohydrate (306 mg, 2.86 mmol), 1-(3-dimethylaminopropyl)-3-ethylcarbodiimide HCl salt (548 mg, 2.86 mmol)and 4-methylmorpholine(0.1 ml, 9.52 mmol)added, and then the solution was stirred at the room temperature overnight. The reaction solution was diluted with ethyl acetate and washed with an aqueous sodium bicarbonate solution, distilled water and a saturated sodium chloride aqueous solution successively. The organic layer was dried over anhydrous sodium sulfate and concentrated under a reduced pressure to give a residue, which was purified by silicagel column chromatography (silicagel 120 g, hexane/ethyl acetate/methanol=10/10/1) to obtain the object compound (488 mg, yield 50%).

1H-NMR (CDCl$_3$); 1.94–2.10 (2H, complex), 2.13 (3H, s), 2.44–2.62 (1H, m), 2.68–2.87 (1H, m), 2.94–3.00 (2H, complex), 3.87 (1H, d, J=3.9 Hz), 4.06–4.10 (1H, m), 4.17–4.30 (2H, complex) 4.32–4.50 (2H, complex), 4.62–4.77 (1H, m) 5.07 (2H, s), 6.40 (1H, d, J=9.3 Hz), 6.64 (1H, br, d, J=8.3 Hz), 6.79–6.87 (1H, m), 7.05–7.28 (5H, overlapped with solvent peak), 7.41–7.57 (6H, complex), 8.0 5–8.10 (2H, complex): MS; m/z=599 (M+1).

(7) 2-(5-acetyloxymethyl-4-oxo-2-phenyl-3,4-dihydropyrimidin-3-yl)-N-{2,3-dioxo-1-phenylmethyl-6-(2-pyridyloxy)}hexylacetamide(Compound No.1):

2-(5-acetyloxymethyl-4-oxo-2-phenyl-3,4-dihydropyrimidin-3-yl)-N-{2-hydroxy-3-oxo-1-phenylmethyl-6-(2-pyridyloxy)} hexylacetamide(154 mg, 0.256 mmol)was dissolved in methylene chloride(0.3 ml)and cooled on ice. To the solution were dimethylsulfoxide(0.27 ml, 3.84 mmol), pyridinium trifluoroacetate(24.7 mg, 0.128 mmol) and 1-(3-dimethylaminopropyl)-3-ethylcarbodiimide HCl salt(147 mg, 0.769 mmol)added, and then the solution was stirred for 3 hrs. The reaction solution was diluted with ethyl acetate and washed with distilled water and a saturated sodium chloride aqueous solution successively. The organic layer was dried over anhydrous sodium sulfate and concentrated under a reduced pressure to give a residue, which was purified by silicagel column chromatography (silicagel 16 g, methylene chloride/ethyl acetate=2/1–1/1) to obtain the object compound (111 mg, yield 73%).

1H-NMR (CDCl$_3$); 2.00–2.15 (3H, complex), 2.75–3.07 (4H, complex), 4.31 (2H, t, J=6.2 Hz), 4.47 (2H, s), 5.06 (2 H, s), 5.2 8–5.38 (1H, m), 6.63 (1 H, br. d, J=6.4 Hz), 6.70 (1H, d, J=8.4Hz), 6.82 −6.89 (1H, m), 7.03–7.24 (5H, overlapped with solvent peak), 7.42–7.60 (6H, complex), 8.07 −8.14 (2H, complex): MS; m/z=597 (M+1)

Example 3

Synthesis of 2-(5-hydroxymethyl-4-oxo-2-phenyl-3,4-dihydropyrimidin-3-yl)-N-{2,3-dioxo-1-phenylmethyl-6-(2-pyridyloxy)} hexylacetamide(Compound No.2) was conducted as described below:

To a solution of 2-(5-acetyloxymethyl-4-oxo-2-phenyl-3, 4-dihydropyrimidin-3-yl)-N-{2,3-dioxo-1-phenylmethyl-6-(2-pyridyloxy)}hexylacetamide(Compound No.1, 30.0 mg, 0.05 mmol) dissolved in 1,4-dioxane(1 ml) was an aqueous 3N HCl solution(1.7 ml, 5 mmol) added, and then the solution was stirred at the room temperature over night. The reaction solution was diluted with ethyl acetate and washed with an aqueous saturated sodium bicarbonate solution. The organic layer was dried over anhydrous sodium sulfate and concentrated under a reduced pressure to obtain the object compound (23 mg, yield 83%).

1H-NMR (CDCl$_3$); 2.03 (1H, m), 2.75–3.34 (4H, complex), 4.29 (2H, t, J=6.2 Hz), 4.46 (2H, S), 4.58 (2H, s), 5.19 –5.30 (1H, m), 6.70 (1H, br. d, J=8.3 Hz), 6.79–6.89 (2H, complex), 7.03–7.24 (5H, complex), 7.43–7.60 (6H, complex), 8.02 (1H, s), 8.08–8.13 (1H, m): MS; m/z=555 (M+1)

Example 4

Synthesis of 2-(5-methoxymethyl-4-oxo-2-phenyl-3,4-dihydropyrimidin-3-yl)-N-{2,3-dioxo-1-phenylmethyl-6-(2-pyridyloxy)} hexylacetamide (Compound No.3) was conducted by the steps as shown below:

(1) 3-allyl-5-methoxymethyl-2-phenyl-3,4-dihydropyrimidine-4-one:

To a solution of 3-allyl-5-hydroxymethyl-2-phenyl-3,4-dihydropyrimidine-4-one(100 mg, 0.413 mmol) dissolved in tetrahydrofuran(1 ml) were methyl iodide(0.3 ml, 2.07 mmol)and sodium hydride(65% in mineral oil, 18 mg, 0.496 mmol) added under the atmosphere of argon gas with cooling on ice, and then the solution was stirred for 1.5 hrs. The reaction solution was diluted with ethyl acetate and washed with a saturated sodium chloride aqueous solution. The organic layer was dried over anhydrous sodium sulfate and concentrated under a reduced pressure to give a residue, which was purified by silicagel column chromatography (silicagel 5 g, hexane/ethyl acetate/methanol=10/10/1) to obtain the object compound (79 mg, yield 75%).

1H-NMR (CDCl$_3$); 3.50 (3H, s) 4.43 (2H, s), 4.55 (2H, m), 4.94 (1H, m), 5.19 (1H, m), 5.78–5.97 (1H, m), 7.48 (5H, complex), 8.05 (1H, br. s): MS; m/z=257 (M+1).

(2) 5-methoxymethyl-2-phenyl-3-(2,3-dihydroxy)propyl-3, 4-di hydropyrimidin-4-one:

3-allyl-5-methoxymethyl-2-phenyl-3,4-dihydropyrimidin-4-one(623 mg, 2.44 mmol) used for a reaction material was treated in the same way as described in the Example 2(3)to obtain the object compound(703 mg, yield 99%).

1H-NMR (CDCl$_3$) 2.66 (1H, t, J=6.6 Hz) 3.29–3.41 (1H, m), 3.50 (3H, s, overlapped with 1H), 3.76 (1H, d, J=5.5 Hz) 4.10–4.15 (2H, complex) 4.43 (2H, d, J=1.1 Hz), 7.41–7.59 (5H, complex) 8.10 (1H, br. s): Ms; m/z=291 (M+1).

(3) 5-methoxymethyl-2-phenyl-3,4-dihydropyrimidin-4-one-3-yl-acetaldehyde:

5-methoxymethyl-2-phenyl-3-(2,3-dihydroxy)propyl-3, 4-di hydropyrimidin-4-one(701 mg, 2.42 mmol) used for a reaction material was treated in the same way as described in the Example 2(4) to obtain the object compound (644 mg, quantitative yield).

1H-NMR (CDCl$_3$); 3.50 (3H, s), 4.43 (2H, d, J=1.1 Hz), 4.74 (2H, s), 7.39–7.54 (5H, complex), 8.10 (1H, br. s), 9.61 (1H, s): MS; m/z=259 (M+1).

(4) 5-methoxymethyl-2-phenyl-3,4-dihydropyrimidin-4-one-3-yl-acetic acid:

5-methoxymethyl-2-phenyl-3,4-dihydropyrimidin-4-one-3-yl-acetaldehyde(643 mg, 2.48 mmol) used for a reaction material was treated in the same way as described in the Example 2(5) to obtain the object compound (898 mg, quantitative yield).

1H-NMR (CDCl$_3$); 3.48 (3H, s), 4.42 (2H, d, J=1.1 Hz), 4.60 (2H, s) 7.50 (5H, br. s), 8.11 (1H, br. s).

(5) 2-(5-methoxymethyl-4-oxo-2-phenyl-3,4-dihydropyrimidin-3-yl)-N-{2-hydroxy-3-oxo-1-phenylmethyl-6-(2-pyridyloxy)}hexylacetamide:

5-methoxymethyl-2-phenyl-3,4-dihydropyrimidin-4-one-3-yl-acetic acid(898 mg, 3.25 mmol)and 2-amino-3-hydroxy-4-oxo-1-phenyl-7-(2-pyridyloxy)heptane 2(p-toluenesulfonic acid)salt(2.27 g, 3.25 mmol) used for reaction materials were treated in the same way as described in the Example 2(6) to obtain the object compound (277 mg, yield 15%).

1H-NMR (CDCl$_3$); 1.80–2.10 (2H, complex), 2.38–2.81 (4H, complex), 3.48 (3H, s), 4.09 (1H, d, J=4.9 Hz), 4.18–4.28 (2H, complex), 4.33–4.45 (5H, complex), 4.62–4.78 (1H, m), 6.62–6.72 (2H, complex), 6.81–6.89 (1H, m), 7.06–7.21 (5H, complex), 7.39–7.60 (6H, complex), 8.07–8.13 (2H, complex): MS; m/z=571 (M+1)

(6) 2-(5-methoxymethyl-4-oxo-2-phenyl-3,4-dihydropyrimidin-3-yl)-N-{2,3-dioxo-1-phenylmethyl-6-(2-pyridyloxy)} hexylacetamide(Compound No.3):

2-(5-methoxymethyl-4-oxo-2-phenyl-3,4-dihydropyrimidin-3-yl)-N-{2-hydroxy-3-oxo-1-phenylmethyl-6-(2-pyridyloxy)}hexylacetamide(50 mg, 0.0876 mmol) used for a reaction material was treated in the same way as described in the Example 2(7) to obtain the object compound (10.2 mg, yield 20%).

1H-NMR (CDCl$_3$); 2.00–2.14 (2H, m), 2.85–3.08 (3H, complex), 3.21 (1H, dd, J=5.6, 14.0 Hz), 3.48 (3H, s), 4.31 (2H, t, J=6.2 Hz) 4.41 (2H, d, J=1.2 Hz), 4.46 (2H, s), 5.25–5.36 (1H, m), 6.61 (1H, br. d, J=6.8 Hz), 6.67–6.73 (1H, m), 6.81–6.89 (1H, m) 7.03–7.25 (5H, complex), 7.44–7.60 (6H, complex), 8.06–8.08 (1H, m), 8.09–8.14 (1H, m): MS; m/z=569 (M+1).

Example 5

Synthesis of 2-(5-ethoxycarbonyl-4-oxo-2-phenyl-3,4-dihydropyrimidin-3-yl)-N-{2,3-dioxo-1-phenylmethyl-6-(2-pyridyloxy)} hexylacetamide (Compound No.4) was conducted by the below steps(1)–(4):

(1) 5-ethoxycarbonyl-2-phenyl-3,4-dihydropyrimidine-4-on-3-yl-acetaldehyde:

3-allyl -5-ethoxycarbonyl-2-phenyl-3,4-dihydropyrimidin-4-one(5.12 g, 18.0 mmol) used for a reaction material was treated in the same way as described in the Example 2(3) to give a residue, which was then, without further purification, treated in the same way as described in the Example 2(4) to obtain the object compound (2.26 g, yield 44%).

Ms; m/z=287 (M+1)

(2) 5-ethoxycarbonyl-2-phenyl-3,4-dihydropyrimidine-4-on-3-yl-acetic acid:

5-ethoxycarbonyl-2-phenyl-3,4-dihydropyrimidin-4-on-3-yl-acetaldehyde(2.26 g, 7.89 mmol) used for a reaction material was treated in the same way as described in the Example 2(5) to obtain the object compound (2.28 g, yield 96%).

MS; m/z=325 (M+Na), 303 (M+1)

(3) 2-(5-ethoxycarbonyl-4-oxo-2-phenyl-3,4-dihydropyrimidin-3-yl)-N-{2-hydroxy-3-oxo-1-phenylmethyl-6-(2-pyridyl-oxy)}hexylacetamide:

5-ethoxycarbonyl-2-phenyl-3,4-dihydropyrimidin-4-one-3-yl-acetic acid(2.21 g, 7.32 mmol)and 2-amino-3-hydroxy-4-oxo-1-phenyl-7-(2-pyridyloxy)heptane 2(p-toluenesulfonic acid)salt(5.06 g, 7.32 mmol) used for reaction materials were treated in the same way as described in the Example 2(6) to obtain the object compound (2.50 g, yield 57%). MS; m/z=599 (M+1)

(4) 2-(5-ethoxycarbonyl-4-oxo-2-phenyl-3,4-dihydropyrimidin-3-yl)-N-{2,3-dioxo-1-phenylmethyl-6-(2-pyridyl-oxy)}hexylacetamide(Compound No.4):

2-(5-ethoxycarbonyl-4-oxo-2-phenyl-3,4-dihydropyrimidin-3-yl)-N-{2-hydroxy-3-oxo-1-phenylmethyl-6-(2-pyridyloxy)}hexylacetamide(413 mg, 0.690 mmol) used for a reaction material was treated in the same way as described in the Example 2 (7) to obtain the object compound (329 mg, yield 80%).

1H-NM R (CDCl$_3$); 1.35 (3H, t, J=7.1 Hz), 2.04 (2H, quint, J=6.7 Hz), 2.82 –3.04 (3H, complex), 3.19 (1H, dd, J=5.6, 14.0 Hz ), 4.23–4.39 (4H, complex), 4.58 (2H, s), 5.18–5.30 (1H, m), 6.68 (1H, br. d, J=8.3 Hz), 6.81–6.88 (1H, m), 6.95 (1H, d, J=6.8 Hz), 7.04–7.10 (2H, complex), 7.15–7.24 (3H, complex), 7.42–7.60 (6H, complex), 8.08–8.13 (1H, m), 8.70 (1H, s): MS; m/z=597 (M+1)

Example 6

Pharmaceutical composition example (Injection):

Purified water was added to 30 parts by weight of the present compound and 18 parts by weight of sodium chloride (100 parts by weight of glucose) to give a total volume of 2000 parts by weight of the solution, which was then filtered through Millipore filter GS type® to remove bacteria. 2 g of the filtrate was pipetted to a vial, which was capped to obtain an injection containing 30 mg of the present compound.

Example 7

Pharmaceutical composition example (Tablets):

10 parts by weight of the present compound, 30 parts by weight of potato starch, 150 parts by weight of crystalline lactose, 108 parts by weight of crystalline cellulose and 2 parts by weight of magnesium stearate were mixed in a V-shaped mixer and tabletted at 60 mg per tablet to give tablets each containing 2 mg of the present compound.

The bioactivity of the present compound will be specifically described below with reference to Test Example.

Test Example

Inhibitory activity on chymase

It is known that chymase is present in tissues of various animals, and its isolation and purification methods are described in Anal. Biochem., 137, 449 (1984) and FEBS Letters, 323, 119 (1993). In the present invention, chymase was purified by the methods described in these literatures, and the present compounds were examined for inhibitory activity on human chymase or dog chymase. The specific methods are as follows:

(A) Preparation of human chymase 60 g human tonsillar gland was finely divided by scissors and a scalpel, suspended in 0.1 M phosphate buffer (pH 8.0), and disrupted by a Polytron homogenizer for 5 minutes to prepare a crude chymase enzyme solution. The solution was centrifuged at 22000×g for 30 min, and the precipitate was used as a chymase enzyme fraction. The precipitate was washed by repeating the above procedure twice, and then suspended in 0.1 M phosphate buffer (pH 8.0) containing 2 M sodium chloride and 5% ammonium sulfate. The suspension was centrifuged at 27000×g for 20 min to give a supernatant as a chymase fraction. The supernatant was concentrated by ultrafiltration, applied to a G2000SW-XL column (6.0×300 mm), and eluted with 0.1 M phosphate buffer (pH 8.0). An active fraction decomposing succinyl leucyl leucyl valyl tyrosyl methylcoumarylamide (hereinafter referred to as the synthetic chymase substrate, made by Peptide Kenkyusho) was recovered, concentrated and used as a purified human chymase for the following activity measurement.

(B) Preparation of dog chymase 60 g dog heart was finely divided by scissors and a scalpel, suspended in 0.1 M phosphate buffer (pH 8.0), and disrupted by a Polytron homogenizer for 5 minutes to prepare a crude chymase enzyme solution. The solution was centrifuged at 22000×g for 15 min, and the precipitate was used as a chymase enzyme fraction. The precipitate was washed by repeating the above procedure twice, and suspended in 0.1 M phosphate buffer (pH 8.0) containing 2 M sodium chloride and 5% ammonium sulfate. The suspension was centrifuged at 27000×g for 40 minutes to give a supernatant as a chymase fraction. The chymase fraction was concentrated by ultrafiltration to remove macromolecules, applied to a Superdex 200HR 10/30 column (10×300 mm), and eluted with 0.1 M phosphate buffer (pH 8.0). An active fraction decomposing the synthetic chymase substrate was recovered, concentrated, and used as a purified dog chymase for the following activity measurement.

(C) Measurement of inhibitory activity on chymase

The inhibitory activity on the human chymase and dog chymase was measured using angiotensin I (made by Peptide Kenkyusho) for a substrate. 200 µl of 0.15 M Tris-HCl buffer (pH 8.0) containing 0.1 mM angiotensin I, 0.0002 µl of human or dog chymase solution and 2 µl of a dimethylsulfoxide solution of the present compound were added into a 1.5 ml test tube and incubated at 37° C. for 15 min. At the end of the reaction, produced angiotensin II was immediately determined by high performance liquid chromatography before measuring the chymase activity to calculate 50% inhibitory concentration (IC50: nM).

The test was conducted several times. Chymase was prepared for each test in the manner described above. The compounds prepared in the above-described Examples were used for the test. The 50% inhibitory concentration (IC50: nM) of each compound on chymase was calculated, and the results are shown in Tables 1 and 2. The compounds tested are listed in Table 3.

TABLE 1

| 50% Inhibitory concentration (IC50: nM) of each compound human chymase | |
|---|---|
| Compound No. | (IC50: nM) |
| 1 | 26 |
| 2 | 27 |
| 3 | 22 |
| 4 | 490 |

TABLE 2

| 50% Inhibitory concentration (IC50: nM) of each compound dog chymase | |
|---|---|
| Compound No. | (IC50: nM) |
| 1 | 3.7 |
| 2 | 2.7 |
| 3 | 2.0 |
| 4 | 52 |

TABLE 3

| Compound No. | $R^0$ | $R^1$ | $R^2$ | J | L | X | Y | Z |
|---|---|---|---|---|---|---|---|---|
| 1 | Ph | Ph | (butoxy-pyridinyl) | —CH$_2$— | AcO | C | N | —CH$_2$— |
| 2 | Ph | Ph | (butoxy-pyridinyl) | —CH$_2$— | HO | C | N | —CH$_2$— |
| 3 | Ph | Ph | (butoxy-pyridinyl) | —CH$_2$— | MeO | C | N | —CH$_2$— |

TABLE 3-continued

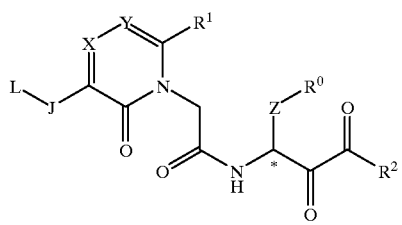

| Compoud No. | R⁰ | R¹ | R² | J | L | X | Y | Z |
|---|---|---|---|---|---|---|---|---|
| 4 | Ph | Ph | (structure: propyl-O-2-pyridyl) | —CO— | EtO | C | N | —CH₂— |

As is evident from Tables 1 and 2, the compounds of the present invention inhibited human chymase and dog chymase at their low concentrations in the test using angiotensin I for a chymase substrate in vivo. Compound 1, Compound 2, and Compound 3 had preferably a powerful inhibitory activity on chymase.

INDUSTRIAL APPLICABILITY

The compounds of the present invention inhibit not only dog chymase but also human chymase at their low concentrations. Further, they also inhibit chymase from converting angiotensin I into angiotensin II, so they are expected as agents for treating or preventing diseases such as asthma, allergy, inflammation, rheumatism, hypertension, heart failure, myocardial infarction, cardiac hypertrophy, vascular injuries complicated with angiogenesis and atheroma, nephritis and renal failure.

What is claimed is:

1. An acetamide derivative represented by the following Formula 1 or the pharmacologically acceptable salt thereof:

Formula 1 wherein $R^0$ is an unsubstituted phenyl group;
$R^1$ is an unsubstituted aryl group;
$R^2$ represents a pyridyl substituent;
X represents a carbon atom and Y represents a nitrogen atom;
Z represents a methylene group;
J represents a carbonyl group, or a methylene group;
L represents $R^3O$ where $R^3$ is a hydrogen; or $R^3$ is (1) $D(CH_2)_{0-3}.CO$, (2) D.CO.E.CO or (3) $D.SO_2.E.CO$ as an acyl group; (wherein group D represents a hydrogen, a 1–6C straight-chain, branched or cyclic alkyl group, trifluoromethyl, 2,2,2,-trifluoroethoxy, amino, methoxyamino, 2,2,2,-trifluoroethylamino, $R_bR_cN$, $R_bR_cN.O$, $R_aO$, $R_a$, $R_aOCO$, $R_bR_cNCO$, $R_aSO_2NR_b$, $R_aS$ and cyclic group G, wherein G represents a heterocyclic group consisting of 5- or 6-membered ring containing 1 to 3 oxygen or nitrogen atoms and may have substituent groups; and group E represents a divalent crosslinking group containing 1 to 6 carbon atoms, and may contain 1–3 hetero atoms selected from the group of oxygen, nitrogen and sulfur); or $R^3$ is an alkyl group.

2. An acetamide derivative of the pharmacologically acceptable salt thereof according to claim 1, wherein said $R^1$ and L in Formula 1 are the respective followings:
$R^1$ is a phenyl group;
L represents $R^3O$ where $R^3$ is hydrogen; or $R^3$ is (1) $D(CH_2)_{0-3}.CO$, (2) D.CO.E.CO or (3) $D.SO_2.E.CO$ as an acyl group; (wherein group D represents a hydrogen, a 1–3C straight-chain, branched or cyclic alkyl group, trifluoromethyl, 2,2,2,-trifluoroethoxy, 2,2,2,-trifluoroethylamino, $COOR_a$, $CONR_bR_c$, $NR_bR_c$, or the above-defined group G; and group E represents a phenylene, a heteroarylene, 1,4-piperazine-di-yl, cyclohexylene, or 1,4-cyclohexa dienylene); or $R^3$ is an alkyl group.

3. An acetamide derivative or the pharmacologically acceptable salt thereof according to claim 1, wherein $R^1$ is a phenyl; $R^2$ represents (2-pyridyloxy)propyl; J represents a methylene group; L represents methoxy, hydroxyl, or acetyloxy.

4. An acetamide derivative or the pharmacologically acceptable salt thereof according to claim 1, wherein $R^1$ is unsubstituted phenyl; $R^2$ is (2-pyridyloxy)propyl;
J is a methylene group; L is a lower alkylcarbonyloxy.

5. An acetamide derivative or the pharmacologically acceptable salt thereof according to claim 1, wherein said acetamide derivative is a compound selected from the group consisting of:
(A) 2-(5-acetyloxymethyl-4-oxo-2-phenyl-3,4-dihydropyrimidin-3-yl)-N-{2,3-dioxo-1-phenylmethyl-6-(2-pyridyloxy)}hexylacetamide,
(B) 2-(5-hydroxymethyl-4-oxo-2-phenyl-3,4-dihydropyrimidin-3-yl)-N-{2,3-dioxo-1-phenylmethyl-6-(2-pyridyloxy)}hexylacetamide,
(C) 2-(5-methoxymethyl-4-oxo-2-phenyl-3,4-dihydropyrimidin-3-yl)-N-{2,3-dioxo-1-phenylmethyl-6-(2-pyridyloxy)}hexylacetamide, (D) 2-(5-ethoxycarbonyl-4-oxo-2-phenyl-3,4-dihydropyrimidin-3-yl)-N-{2,3-dioxo-1-phenylmethyl-6-(2-pyridyloxy)}hexylacetamide, (E) 2-(5-acetylaminomethyl-4-oxo-2-phenyl-3,4-dihydropyrimidin-3-N-{2,3-dioxo-1-phenylmethyl-6-(2-pyridyloxy)}hexylacetamide.

6. A salt of the novel acetamide derivative according to claim 1, wherein said salt is (A) selected from the group consisting of the alkali metal salt, the alkaline earth metal salt, the aluminum salt, the ammonium salt and the salt obtained by reacting with an organic base forming the pharmaceutically acceptable cations, if the novel acetamide derivative of Formula 1 is an acidic compound, or (B) selected from the group consisting of acid addition salts obtained by reacting with acids forming the pharmaceutically acceptable anions, if the novel acetamide derivatives of Formula 1 is a basic compound.

7. A process for producing the acetamide derivative according to any of claims 1 to 6 or the pharmacologically acceptable salt thereof, which comprises the following step (A):

(A) in synthesis of the acetamide derivatives of Formula 1, the step of oxidizing the alcohol compound of Formula 2:

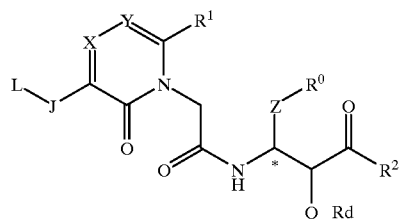

Formula 2 after removal of a protective group of alcohol if present, to convert it into the acetamide derivative of Formula 1 (wherein Rd represents a hydrogen or a protective group for hydroxyl group).

8. A pharmaceutical composition comprising the novel acetamide derivative according to any of claims 1 to 6 or the pharmacologically acceptable salt thereof as an active ingredient.

9. An antiathmatic agent, an antiallergic agent, an antiinflammatory agent an antirheumatic agent, an antihypertensive agent, an anti-heart failure agent, an anti-myocardial infarction agent, a remedy for cardiac hypertrophy or vascular injuries complicated with angiogenesis or atheroma, an anti-nephritis agent, an anti-renal failure agent, or their prophylactic agents comprising the novel acetamide derivative according to any of claims 1 to 6 or the pharmacologically acceptable salt thereof as an active ingredient.

* * * * *